(12) United States Patent
Zaitsu et al.

(10) Patent No.: US 10,156,540 B2
(45) Date of Patent: Dec. 18, 2018

(54) TEST STRIP FOR BIOLOGICAL COMPONENT MEASUREMENT AND MANUFACTURING METHOD THEREOF

(71) Applicant: OMRON HEALTHCARE CO., LTD., Muko-shi, Kyoto (JP)

(72) Inventors: Kenichiro Zaitsu, Kyoto (JP); Muneo Tokita, Kyoto (JP); Satoshi Nakajima, Kyoto (JP)

(73) Assignee: OMRON HEALTHCARE CO., LTD., Muko (JP)

( * ) Notice: Subject to any disclaimer, the term of this patent is extended or adjusted under 35 U.S.C. 154(b) by 646 days.

(21) Appl. No.: 14/724,422

(22) Filed: May 28, 2015

(65) Prior Publication Data

US 2015/0260676 A1     Sep. 17, 2015

Related U.S. Application Data

(63) Continuation of application No. PCT/JP2013/080973, filed on Nov. 18, 2013.

(30) Foreign Application Priority Data

Dec. 14, 2012  (JP) .................................. 2012-273838

(51) Int. Cl.
  *G01N 27/327*    (2006.01)
  *G01N 33/487*    (2006.01)

(52) U.S. Cl.
  CPC ... *G01N 27/3272* (2013.01); *G01N 33/48771* (2013.01)

(58) Field of Classification Search
  CPC ................. G01N 27/3272; G01N 33/48771
  See application file for complete search history.

(56) References Cited

U.S. PATENT DOCUMENTS 8,888,973 B2 *  11/2014  Austera ............. G01N 27/3272
                                                    204/403.02
2004/0244151 A1 * 12/2004  Sakata ............ G01N 33/48771
                                                    23/306

FOREIGN PATENT DOCUMENTS

| JP | 2001-311711 A | 11/2001 |
| JP | 2001-356108 A | 12/2001 |
| JP | 2002-156358 A | 5/2002 |

(Continued)

OTHER PUBLICATIONS

Jan. 28, 2014 International Search Report issued in International Patent Application No. PCT/JP2013/080973.

*Primary Examiner* — J. Christopher Ball
(74) *Attorney, Agent, or Firm* — Oliff PLC

(57) ABSTRACT

A test strip for biological component measurement includes a substrate. A pair of a working electrode and a counter electrode, a sensor unit that produces an electrochemical reaction with a bodily fluid of a measurement subject and produces a change in electrical characteristics, a resistance portion having an electrical resistance expressing attribute information including a sensitivity of the test strip, and a pair of wires connected to both ends of the resistance portion are provided on the substrate. The resistance portion has a plurality of narrow patterns, each having a resistivity and provided so as to be distanced from each other. An end portion of each narrow pattern is near another narrow pattern. A substantially circular pattern is provided to overlap locations where the end portions of the narrow patterns are near each other, enabling the end portions to conduct with each other.

18 Claims, 19 Drawing Sheets

(56) References Cited

FOREIGN PATENT DOCUMENTS

| | | | |
|---|---|---|---|
| JP | 2006-015068 A | | 1/2006 |
| JP | 2007-524819 A | | 8/2007 |
| JP | 4264478 B2 | | 5/2009 |
| JP | 4845958 B2 | | 12/2011 |
| KR | 1020090074639 | * | 2/2011 |
| WO | 03/012421 A1 | | 2/2003 |

* cited by examiner

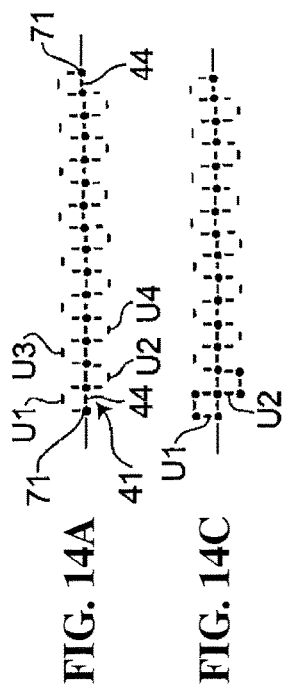
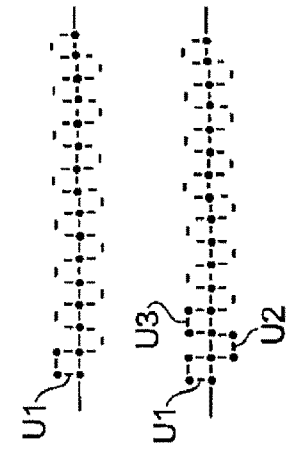
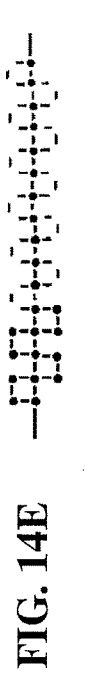
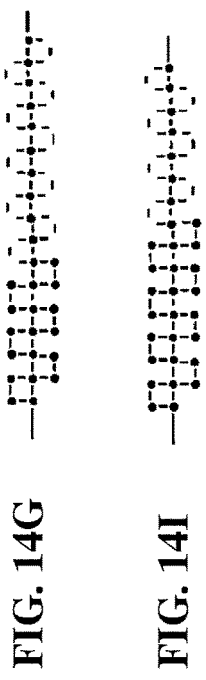
FIG. 14A FIG. 14B FIG. 14C FIG. 14D FIG. 14E FIG. 14F FIG. 14G FIG. 14H FIG. 14I FIG. 14J FIG. 14K FIG. 14L FIG. 14M FIG. 14N FIG. 14O FIG. 14P

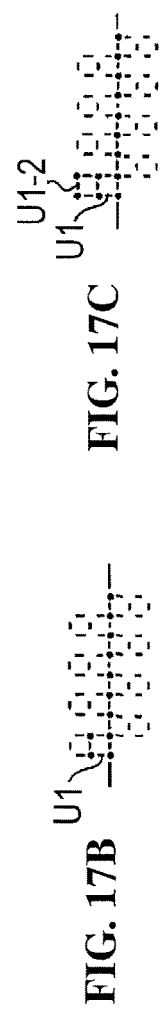
FIG. 17A
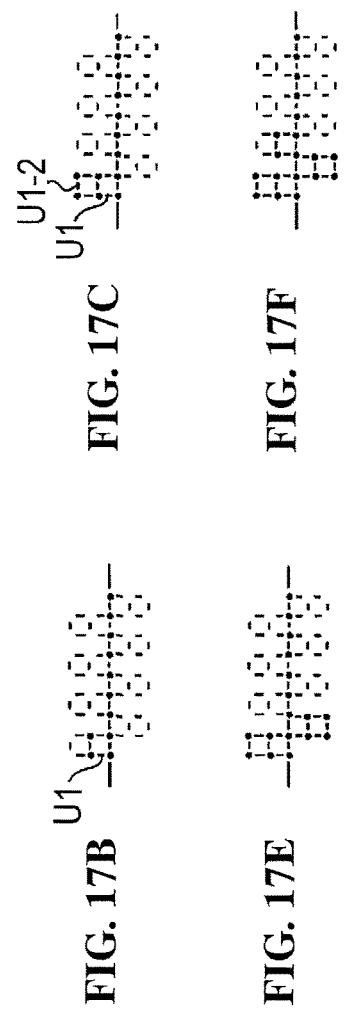
FIG. 17B
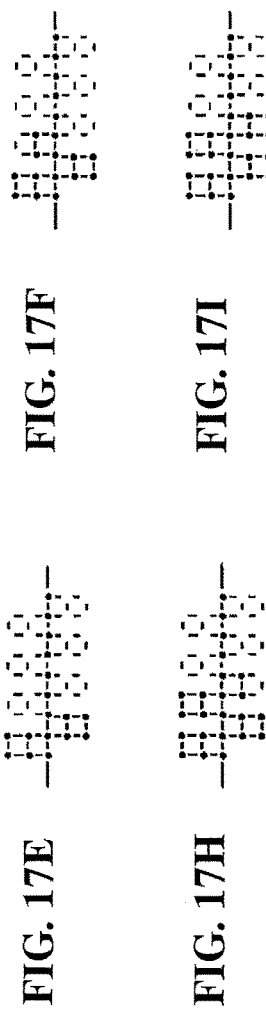
FIG. 17C
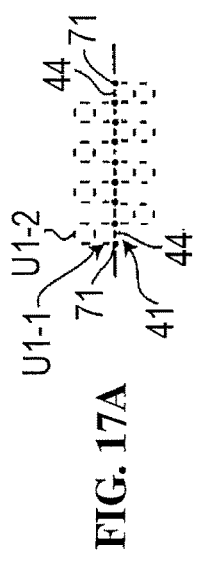
FIG. 17D
FIG. 17E
FIG. 17F
FIG. 17G
FIG. 17H
FIG. 17I
FIG. 17J
FIG. 17K
FIG. 17L
FIG. 17M
FIG. 17N
FIG. 17O
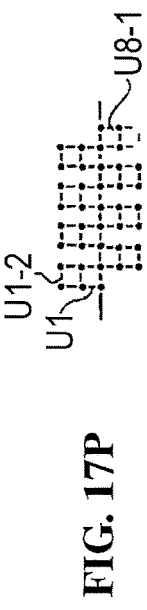
FIG. 17P

TEST STRIP FOR BIOLOGICAL COMPONENT MEASUREMENT AND MANUFACTURING METHOD THEREOF

TECHNICAL FIELD

This invention relates to test strips for biological component measurement, and particularly relates to test strips on which a bodily fluid of a measurement subject is deposited in order to measure the concentration of a specific component in the bodily fluid.

This invention also relates to test strip manufacturing methods for manufacturing such a test strip.

BACKGROUND ART

The test strip disclosed in Patent Literature 1 (Japanese Patent No. 4,264,478), for example, has been disclosed thus far as this type of test strip for biological component measurement. The test strip (biosensor) according to Patent Literature 1 includes a rectangular substrate, a working electrode and a counter electrode that are provided on a top surface of the substrate, separated from each other and extending along a longer direction of the substrate, a reagent portion formed at one end portion of the substrate so as to bridge a gap between the working electrode and the counter electrode, and a spacer and a cover provided on the substrate so as to form a channel from the one end portion of the substrate to the reagent portion. Furthermore, an attribute information output unit that outputs attribute information of the test strip (information for selecting a calibration curve that matches a sensitivity, a measurement item, or the like, for example) is provided on the top surface of the substrate between the working electrode and the counter electrode. At the other end portion of the substrate, the working electrode and the counter electrode each has an electrode terminal for making contact with respective contact points (terminal portions) in a measurement device main body (a concentration measurement device), and the attribute information output unit is provided with a plurality of lead portions for outputting the attribute information.

The attribute information output unit is formed by setting a cutting candidate area and varying a resistance value of the attribute information output unit by cutting the cutting candidate area by machining the area using a drill, laser processing, or etching, for example.

During measurement, a measurement subject's bodily fluid is deposited on the one end portion of the test strip (the substrate), and the other end portion of the substrate (the electrode terminals of the working electrode and the counter electrode) makes contact with the contact points provided in the measurement device main body.

The bodily fluid deposited on the one end portion of the substrate reaches the reagent portion through the flow channel due to the capillary phenomenon, and electrical properties between the working electrode and the counter electrode change due to an electrochemical reaction. The measurement device main body measures a response current value of the reagent portion resulting from a voltage applied thereto via the working electrode and the counter electrode on the substrate, and obtains the attribute information outputted from the attribute information output unit via the plurality of lead portions. The measurement device main body calculates the concentration of a specific component in the bodily fluid based on the response current value and the calibration curve selected based on the attribute information.

Through this, an inaccurate concentration measurement can be prevented even if the sensitivity varies from test strip to test strip.

CITATION LIST

Patent Literature

Patent Literature 1: Japanese Patent No. 4,264,478
Patent Literature 2: Japanese Patent No. 4,845,958

SUMMARY OF INVENTION

Technical Problem

However, in the test strip, forming the attribute information output unit by cutting the cutting candidate area by machining the area using a drill, laser processing, or etching results in the following problems:
i) equipment costs for machining, laser processing, or etching are high, resulting in a high cost of manufacture for the test strip; and
ii) particularly in the case of machining and laser processing, cutting the cutting candidate area produces debris that re-adheres to the test strip and soils the test strip, properties of the reagent portion (sensor unit) are affected by heat produced during processing, and other such causes of drops in quality occur.

Note that Patent Literature 2 (Japanese Patent No. 4,845,958) discloses a technique for variably setting a resistance value used for calibration by changing a printing pattern. However, according to this technique, it is necessary to prepare multiple types of printing plates for the printing pattern, resulting in a problem that the cost of manufacture of the test strip increases.

Accordingly, it is an advantage of this invention to provide a test strip for biological component measurement, on which a measurement subject's bodily fluid is deposited in order to measure a concentration of a specific component in the bodily fluid, that can be manufactured at a low cost and with a high quality.

It is a further advantage of this invention to provide a manufacturing method of a test strip for biological component measurement, on which a measurement subject's bodily fluid is deposited in order to measure a concentration of a specific component in the bodily fluid, that enables the test strip to be manufactured at a low cost and with a high quality.

Solution to Problem

To solve the aforementioned problem, according to a first aspect, a test strip according to this invention is a test strip for biological component measurement that is to be mounted in a measurement device main body and on which a bodily fluid of a measurement subject is to be deposited in order to measure a concentration of a specific component in the bodily fluid, the test strip including a substrate, the substrate having thereon a pair of a working electrode and a counter electrode extending in one direction while being distanced from each other, a sensor unit, formed so as to span a space between the working electrode and the counter electrode toward one end portion in the one direction, configured to produce an electrochemical reaction with the bodily fluid of the measurement subject and produce a change in electrical characteristics; a resistance portion, formed between both end portions in the one direction and in a region between the pair of the working electrode and the counter electrode, having an electrical resistance expressing attribute information including a sensitivity of the test strip; and a pair of wires connected to both ends of the resistance portion. The pair of the working electrode and the counter electrode and the pair of the wires respectively have a first pair of electrode terminals and a second pair of electrode terminals configured to make contact with contact points provided in the measurement device main body at another end portion on the side opposite from the one end portion in the one direction. The resistance portion has a plurality of narrow patterns, each having an resistivity and provided so as to be distanced from each other, an end portion of each narrow pattern being near an end portion of another narrow pattern, and substantially circular circular patterns provided so as to overlap locations where the end portions of the narrow patterns are near each other and configured to enable the end portions to conduct with each other. A substantially plate-shaped spacer and a flat cover are further provided on the substrate; toward the one end portion in the one direction, the spacer forms side walls that oppose each other on both sides of the sensor unit and the cover covering the sensor unit across the side walls of the spacer that oppose each other so as to define an amount of the bodily fluid that makes contact with the sensor unit on the substrate; the first pair and second pair of electrode terminals are exposed from the spacer and the cover at the other end portion in the one direction; and the spacer and the cover have an opening that exposes the resistance portion in a region corresponding to the resistance portion between both of the end portions in the one direction.

In the present specification, the specific component of the bodily fluid of the measurement subject refers to blood sugar (glucose), cholesterol, lactic acid, or the like, for example.

The "contact points" in the measurement device main body refers broadly to members that make contact and conduct with the electrode terminals of the test strip, regardless of whether the contact points are referred to as "contact points", "terminals", "electrodes", "electrode terminals", or the like.

A "change in electrical characteristics" of the sensor unit includes an electromotive current being produced, an electrical resistance changing from an infinite value to a finite value, and so on.

Furthermore, "attribute information" of the test strip can include, for example, information expressing a sensitivity of the sensor unit of the test strip (for example, a correspondence relationship between the concentration of the specific component in the bodily fluid and the electromotive current produced by the sensor unit), information for selecting a calibration curve that matches the component to be measured, and so on.

Meanwhile, the "end portions" of the narrow patterns refer to end portions in the longer direction. End portions of the narrow patterns being "near" each other refers to the end portions being nearer to each other than portions of the narrow patterns aside from the end portions (these will be referred to as "active portions").

Meanwhile, the circular patterns being "substantially circular" includes not only perfect circles, but also circles that are elongated due to manufacturing variation and the like, for example.

According to the test strip of this invention, the plurality of narrow patterns of the resistance portion can be formed in the manufacturing stage at once through screen printing, for example, using a single printing plate before, for example, the sensor unit is formed, even in the case where the electrical resistance for the resistance portion as a whole is set to be variable in order to express the attribute information including the sensitivity of the test strip. In other words, it is not necessary to change the printing plate. In addition, the circular patterns in the resistance portion can be formed through potting, for example, by dripping a conductive material and then drying the material, after the sensor unit has been formed and the electrical resistance (attribute information) the resistance portion is to have has been found. At this time, by selecting the end portions of the narrow patterns that are near each other, the electrical resistance of the resistance portion is set to be variable in order to have the electrical resistance (express the attribute information) found for the resistance portion as a whole.

In such a case, expensive equipment is unnecessary, and it is also not necessary to prepare multiple types of printing plates. Accordingly, the cost of manufacture of the test strip can be kept low. In addition, the test strip will not be soiled by debris, and the properties of the sensor unit will not be affected by heat produced during processing after the sensor unit has been formed. Accordingly, the test strip can be manufactured having a high quality.

Note that the electrical resistance of the resistance portion is measured through the pair of wires including the second pair of electrode terminals in the case where the concentration of a specific component in the measurement subject's bodily fluid is measured using this test strip. Through this, the attribute information, including the sensitivity, of the test strip is obtained. On the other hand, when the measurement subject's bodily fluid is deposited on the sensor unit, the electrical characteristics of the sensor unit are measured through the pair of the working electrode and the counter electrode including the first pair of electrode terminals. The concentration of the specific component in the bodily fluid is found based on the measured electrical characteristics of the sensor unit and the attribute information.

In this test strip, the amount of the bodily fluid that makes contact with the sensor unit on the substrate is regulated by the spacer and the cover. In particular, the resistance portion is exposed through the opening in the spacer and the cover. Accordingly, the concentration can be measured accurately. On the other hand, the first pair and second pair of electrode terminals and the resistance portion are exposed on the substrate from the spacer and the cover. Accordingly, it is easy to adjust and set the electrical resistance of the resistance portion based on the sensitivity of the sensor unit at the manufacturing stage, after the spacer and the cover have been provided on the substrate and the electrical characteristics of the test strip have been determined. Accordingly, the electrical resistance of the resistance portion can accurately express the attribute information of the test strip, and in particular the sensitivity of the sensor unit.

The test strip according to another embodiment further includes an insulating layer configured to cover active portions of the narrow patterns aside from the end portions thereof and that includes circular through-holes that define borders of the circular patterns.

In the test strip according to this embodiment, the active portions of the narrow patterns aside from the end portions are covered by the insulating layer. Accordingly, the electrical resistance of the active portions of the narrow patterns contribute to the electrical resistance of the resistance portion as a whole with certainty. In addition, the borders of the circular patterns are defined by the circular through-holes in the insulating layer at the manufacturing stage, and thus the shapes of the circular patterns can be formed with a high level of precision. The precision of the electrical resistance of the resistance portion as a whole is further improved as a result. Accordingly, the test strip can be manufactured having an even higher quality.

In the test strip according to another embodiment, each of the circular patterns in the resistance portion is formed through potting and has a surface bent in a convex manner in a direction opposite from the substrate.

In the test strip according to this embodiment, each of the circular patterns in the resistance portion has a surface bent in a convex manner in a direction opposite from the substrate, and thus the thickness thereof can be ensured with ease. Accordingly, if the circular patterns are formed of a typical conductive material, the end portions of the narrow patterns that are near each other can be substantially shorted. As a result, only the electrical resistance of the active portions of the narrow patterns substantially contributes to the electrical resistance of the resistance portion as a whole. The precision of the electrical resistance of the resistance portion as a whole is improved as a result. Accordingly, the test strip can be manufactured having an even higher quality.

In the test strip according to another embodiment, a length and a cross-sectional area of the active portions of the plurality of narrow patterns aside from the end portions thereof are the same.

In the present specification, the "length" of the active portions of the narrow patterns refers to a dimension in the longer direction thereof. Meanwhile, the "cross-sectional area" of the active portions of the narrow patterns refers to an area of a cross-section perpendicular to the longer direction.

In the test strip according to this embodiment, the length and the cross-sectional area of the active portions of the plurality of narrow patterns aside from the end portions thereof are the same, and thus the plurality of narrow patterns have the same electrical resistance. Accordingly, the electrical resistance of the resistance portion as a whole is constituted by serial or parallel combinations of the same electrical resistance (this will be called a "unit resistance"). As a result, in the manufacturing stage, when varying and setting the electrical resistance of the resistance portion so as to express the attribute information of the resistance portion as a whole, the end portions of the narrow patterns that are near each other can be selected with ease.

In the test strip according to another embodiment, the plurality of narrow patterns are arranged so as to form respective segments of a substantially square grid, and at each of grid points in the square grid, a gap is present between respective end portions of the narrow patterns that are near each other.

In the present specification, "grid point" does not refer strictly to a point lacking surface area, but is a concept indicating a region where respective narrow patterns intersect with each other having a width (a dimension in a direction perpendicular to the longer direction).

In the test strip according to this embodiment, the plurality of narrow patterns are arranged so as to form respective segments of a substantially square grid, and thus the narrow patterns can be laid out with ease. For example, when manufacturing a printing plate for a screen printing method, it is easy to design the plate.

In the test strip according to another embodiment, the gap between the respective end portions of the narrow patterns that are near each other is a gap having a constant dimension in a width direction that is orthogonal to a longer direction of the narrow patterns.

In the test strip according to this embodiment, the gap between the respective end portions of the narrow patterns that are near each other is a gap having a constant dimension in the width direction that is orthogonal to the longer direction of the narrow patterns. Accordingly, in the manufacturing stage, when forming the circular patterns so as to overlap with the end portions of the narrow patterns that are near each other (called "grid points" hereinafter for the sake of simplicity), the dimensions of the circular patterns (and/or the circular through-holes) can be made comparatively small in accordance with the gap that has a constant dimension. For example, when forming the circular patterns through potting, a size of a droplet of a conductive material that forms the circular patterns can be set to be comparatively smaller. As a result, the shapes of the circular patterns can be formed with an even higher degree of precision. Accordingly, the test strip can be manufactured having an even higher quality.

In the test strip according to another embodiment, the arrangement of the plurality of narrow patterns forms a plurality of segments arranged in a single row along a longer direction of the substrate, and forms unit grids, on both sides of the single row, that each contains corresponding segments and that are arranged along the longer direction in an alternating manner, and both ends of the segments arranged in the single row as a whole are conductive with the pair of wires.

In the test strip according to this embodiment, in the manufacturing stage, when varying and setting the electrical resistance of the resistance portion so as to express the attribute information of the resistance portion as a whole, the end portions of the narrow patterns that are near each other can be selected with ease.

For example, the electrical resistance of the resistance portion is set to be variable in the following manner.

First, all of the grid points on segments arranged along the single row are selected and made conductive by the circular patterns in order to obtain a comparatively high resistance value for the resistance portion as a whole. For example, when the number of segments arranged along the single row is expressed as m (where m is a natural number of 2 or greater) and the unit resistance of the active portion of each segment in the narrow patterns is expressed as Ra, the resistance value of the resistance portion as a whole is m×Ra.

Furthermore, if a unit grid on one side of one segment contained in the single row is made conductive, or in other words, if each grid point at two corner portions distanced from the one segment of the unit grid is made conductive, the contribution of that unit grid will be:

$$\frac{1}{\frac{1}{Ra}+\frac{1}{3Ra}} = \frac{3}{4}Ra$$

Accordingly, the resistance value of the resistance portion as a whole will be (m−¼)Ra.

Furthermore, if the unit grids on one side (or the other side) of i (where i is an integer in which 0≤i≤m holds true) segments contained in the single row are made conductive, the resistance value of the resistance portion as a whole is (m−i/4)Ra.

In this case, (m+1) values can be set in a variable manner, in 0.25 Ra steps, for the electrical resistance of the resistance portion. At this time, it is sufficient to set whether or not the unit grids on one side (or the other side) of the segments contained in the single row are made conductive in order for the resistance portion to express the attribute information as a whole. Accordingly, the end portions of the narrow patterns that are near each other can be selected with ease, and the electrical resistance of the resistance portion can be set in a variable manner so that the resistance portion expresses the attribute information as a whole.

In the test strip according to another embodiment, the arrangement of the plurality of narrow patterns has other unit grids that make contact with the opposite side of the segments arranged in a single row from the side on which the aforementioned unit grids are located.

In the test strip according to this embodiment, when the number of segments arranged in the single row is expressed as m, (2m+1) values can be set so as to be variable in stages. In other words, the number of variations that can be made on the electrical resistance of the resistance portion is greater than in the case where one unit grid is arranged on each side of the single row. Accordingly, a variety of attribute information can be expressed by the electrical resistance of the resistance portion. Conversely, if the number of variations on the electrical resistance of the resistance portion that is to be set is considered, the number m of segments arranged in the single row can be reduced as compared to the case where one unit grid is arranged on each side of the single row. This means that a dimension of the region of the substrate occupied by the resistance portion can be reduced in the direction of the single row. Accordingly, the resistance portion can be laid out with more freedom on the substrate.

In the test strip according to another embodiment, one of the terminals in the first pair of electrode terminals and one of the terminals in the second pair of electrode terminals are formed in common.

In the test strip according to this embodiment, one of the terminals in the first pair of electrode terminals and one of the terminals in the second pair of electrode terminals are formed in common. The number of electrode terminals can thus be reduced as compared to a case where the first pair of electrode terminals and the second pair of electrode terminals are formed separately. This makes it possible to relax a requirement for dimensional precision when disposing the electrode terminals. As such, the test strip can be manufactured with ease.

According to a second aspect, a manufacturing method of a test strip according to this invention is a manufacturing method of a test strip for manufacturing the aforementioned test strip according to the first aspect, and includes: forming the pair of the working electrode and the counter electrode and the pair of wires on the substrate; forming the narrow patterns of the resistance portion on the substrate through screen printing; forming the sensor unit so as to span the space between the working electrode and the counter electrode; and after providing the spacer and the cover on the substrate in that order, so that the spacer forms side walls that oppose each other on both sides of the sensor unit toward the one end portion in the one direction and the cover covers the sensor unit across the side walls of the spacer that oppose each other so as to define an amount of the bodily fluid that makes contact with the sensor unit on the substrate, and so that the first pair and the second pair of electrode terminals are exposed from the spacer and the cover toward the other end portion in the one direction and the resistance portion is exposed through the opening in the spacer and the cover in a region between both of the end portions in the one direction, finding an electrical resistance the resistance portion is to have as the attribute information including the sensitivity of the test strip by causing the sensor unit to operate; and selecting the end portions of the narrow patterns that are close to each other so that the resistance portion as a whole has the electrical resistance that has been found, and then forming the circular patterns through potting so as to overlap with the selected end portions.

According to the manufacturing method of a test strip of this invention, the plurality of narrow patterns of the resistance portion can be formed at once through screen printing, for example, using a single printing plate before, for example, the sensor unit is formed, even in the case where the electrical resistance for the resistance portion as a whole is set to be variable in order to express the attribute information including the sensitivity of the test strip. In other words, it is not necessary to change the printing plate. In addition, the circular patterns in the resistance portion can be formed through potting (dripping a conductive material and then drying the material) after the sensor unit has been formed and the electrical resistance (attribute information) the resistance portion is to have has been found. At this time, by selecting the end portions of the narrow patterns that are near each other, the electrical resistance of the resistance portion is set to be variable in order to have the electrical resistance (express the attribute information) found for the resistance portion as a whole.

In such a case, according to this manufacturing method of a test strip, expensive equipment is unnecessary, and it is also not necessary to prepare multiple types of printing plates. Accordingly, the cost of manufacture of the test strip can be kept low. In addition, the test strip will not be soiled by debris, and the properties of the sensor unit will not be affected by heat produced during processing after the sensor unit has been formed. Accordingly, the test strip can be manufactured having a high quality.

In this manufacturing method of a test strip, the amount of the bodily fluid that makes contact with the sensor unit on the substrate is regulated by the spacer and the cover. Accordingly, the manufactured test strip can measure the concentration accurately. On the other hand, the first pair and second pair of electrode terminals and the resistance portion are exposed on the substrate from the spacer and the cover. In particular, the resistance portion is exposed through the opening in the spacer and the cover. Accordingly, it is easy to adjust and set the electrical resistance of the resistance portion based on the sensitivity of the sensor unit at the manufacturing stage, after the spacer and the cover have been provided on the substrate and the electrical characteristics of the test strip have been determined. Accordingly, the electrical resistance of the resistance portion can accurately express the attribute information of the manufactured test strip, and in particular the sensitivity of the sensor unit.

In the manufacturing method of a test strip according to another embodiment, after forming the narrow patterns of the resistance portion and before forming the sensor unit, an insulating layer configured to cover active portions of the narrow patterns aside from the end portions thereof and that includes circular through-holes that define borders of the circular patterns is formed.

In the manufacturing method of a test strip according to this embodiment, the active portions of the narrow patterns aside from the end portions are covered by the insulating layer. Accordingly, the electrical resistance of the active portions of the narrow patterns contribute to the electrical resistance of the resistance portion as a whole with certainty. In addition, the borders of the circular patterns are defined by the circular through-holes in the insulating layer, and thus the shapes of the circular patterns can be formed with a high level of precision. The precision of the electrical resistance of the resistance portion as a whole is further improved as a result. Meanwhile, the insulating layer is formed before the sensor unit is formed, and thus the process of forming the insulating layer does not affect the properties of the sensor unit. Accordingly, the test strip can be manufactured having an even higher quality.

In addition, according to a third aspect, a test strip according to this invention is a test strip for biological component measurement that is to be mounted in a measurement device main body and on which a bodily fluid of a measurement subject is to be deposited in order to measure a concentration of a specific component in the bodily fluid, the test strip including a substrate, the substrate having thereon a pair of a working electrode and a counter electrode extending while being distanced from each other; a sensor unit, formed so as to span a space between the working electrode and the counter electrode, configured to produce an electrochemical reaction with the bodily fluid of the measurement subject and produce a change in electrical characteristics; a resistance portion having an electrical resistance expressing attribute information including a sensitivity of the test strip; and a pair of wires connected to both ends of the resistance portion. The pair of the working electrode and the counter electrode and the pair of the wires respectively have a first pair of electrode terminals and a second pair of electrode terminals configured to make contact with contact points provided in the measurement device main body. The resistance portion has a plurality of narrow patterns, each having an resistivity and provided so as to be distanced from each other, an end portion of each narrow pattern being near an end portion of another narrow pattern; and substantially circular circular patterns provided so as to overlap locations where the end portions of the narrow patterns are near each other and configured to enable the end portions to conduct with each other. The test strip further includes an insulating layer configured to cover active portions of the narrow patterns aside from the end portions thereof and that includes circular through-holes that define borders of the circular patterns.

In addition, according to a fourth aspect, a manufacturing method of a test strip is a manufacturing method of a test strip for manufacturing the test strip according to the aforementioned third aspect, the method including: forming the pair of the working electrode and the counter electrode and the pair of wires on the substrate; forming the narrow patterns of the resistance portion through screen printing and forming the insulating layer that covers the active portions of the narrow patterns aside from the end portions and that has the circular through-holes on the substrate in that order; forming the sensor unit so as to span the space between the working electrode and the counter electrode; and after finding an electrical resistance the resistance portion is to have as the attribute information including the sensitivity of the test strip by causing the sensor unit to operate, selecting the end portions of the narrow patterns that are close to each other so that the resistance portion as a whole has the electrical resistance that has been found, and then forming the circular patterns through potting so as to overlap with the selected end portions and serve as borders of the circular through-holes in the insulating layer.

Advantageous Effects of Invention

As is clear from the foregoing, the test strip for biological component measurement according to this invention can be manufactured at a low cost and with a high quality.

In addition, according to the manufacturing method of a test strip according to this invention, a test strip for biological component measurement, on which a measurement subject's bodily fluid is deposited in order to measure a concentration of a specific component in the bodily fluid, can be manufactured at a low cost and with a high quality.

BRIEF DESCRIPTION OF DRAWINGS

FIGS. 14A to 14P are diagrams illustrating various states a resistance portion of the stated test strip can take on when an electrical resistance the resistance portion is set among 16 stages.

FIGS. 17A to 17P are diagrams illustrating various states a resistance portion of the test strip according to the stated variation can take on when an electrical resistance the resistance portion is set among 16 stages.

DESCRIPTION OF EMBODIMENTS

Hereinafter, an embodiment of the invention will be described in detail with reference to the drawings.

Figure 1:
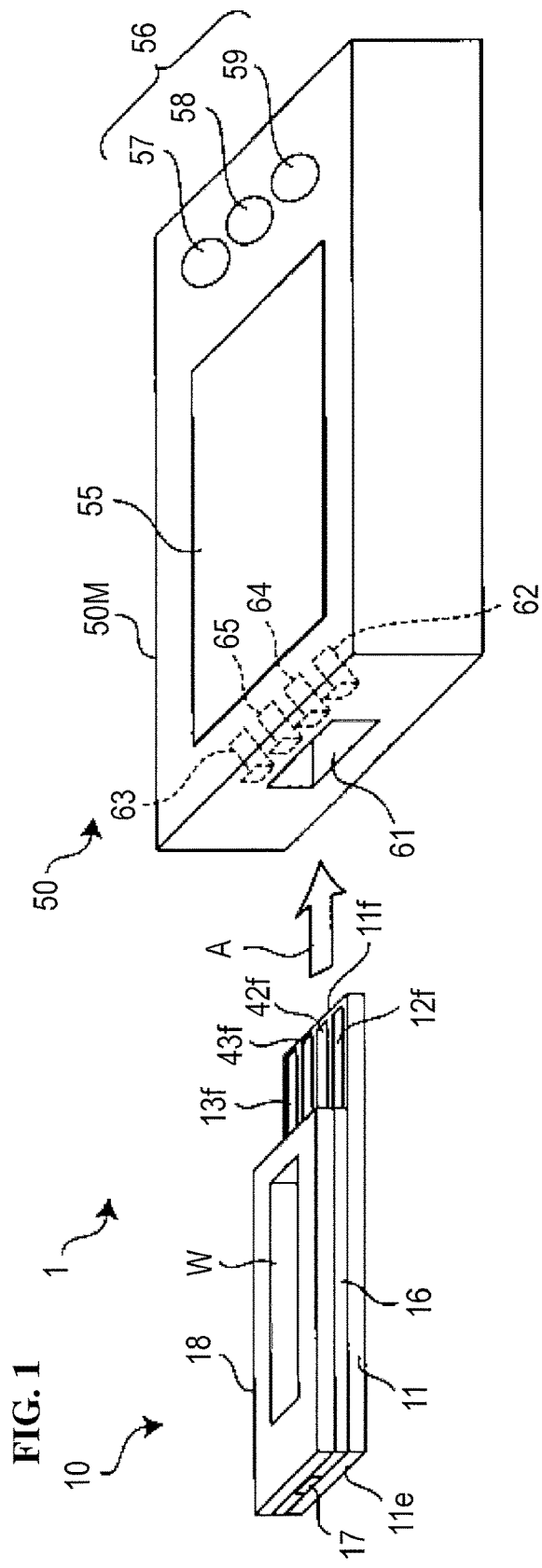
FIG. 1 is a perspective view illustrating a biological component measurement device, including a test strip for biological component measurement and a measurement device main body in which the test strip is mounted, according to an embodiment of this invention.

FIG. 1 illustrates a biological component measurement device (indicated overall by reference numeral 1) from an angle. This biological component measurement device 1 broadly includes a test strip 10, according to this embodiment of the invention, on which a bodily fluid of a measurement subject is deposited in order to measure the concentration of a specific component in the bodily fluid, and a measurement device main body (called simply a "main body" hereinafter) 50 in which the test strip 10 is mounted. Blood sugar (glucose), cholesterol, lactic acid, and so on can be given as examples of the specific component in the bodily fluid.

Configuration of Test Strip

Figure 2:
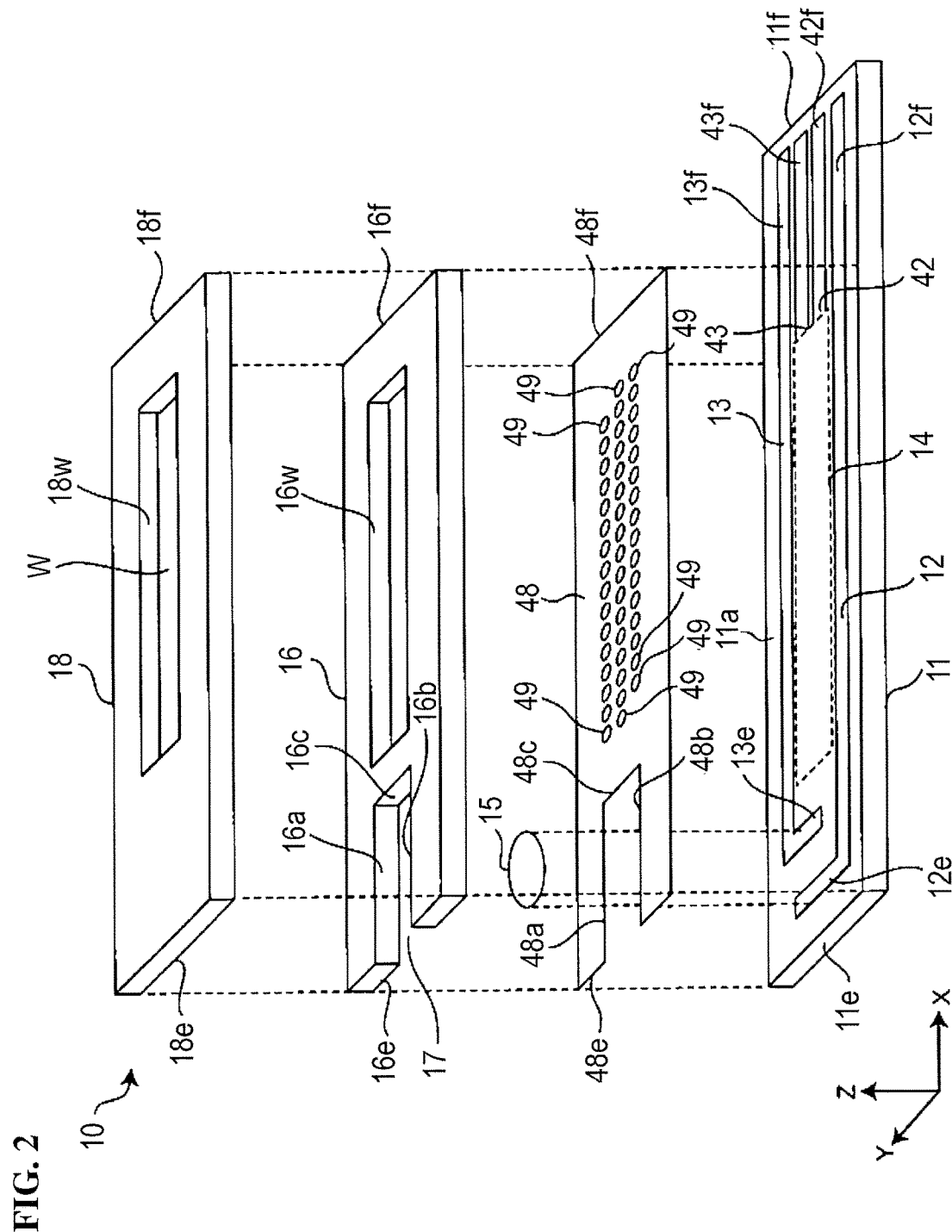
FIG. 2 is a diagram illustrating the stated test strip in an exploded state.

As can be clearly seen in FIG. 2 (which illustrates an exploded state), the test strip 10 includes a substrate 11, a resist layer 48 serving as an insulating layer, a spacer 16, and a cover sheet 18. Note that FIG. 2 also illustrates an XYZ orthogonal coordinate system.

In this example, the substrate 11 is constituted by an insulative plastic material, and has a narrow rectangular shape that extends in one direction (an X direction, in FIG. 2).

A working electrode 12 and a counter electrode 13 that form a pair are provided on a top surface 11a (a surface on a +Z side in FIG. 2) of the substrate 11, so as to be distanced from each other and extend in narrow band shapes along the X direction. The working electrode 12 and the counter electrode 13 are formed by screen-printing a conductive carbon paste or the like. The working electrode 12 and the counter electrode 13 bend in +Y and −Y directions, respectively, which are perpendicular to the X direction, in a region toward one end portion 11e of the substrate 11 (a −X side) in the X direction, and thus have overall L shapes. In a region toward another end portion 11f of the substrate 11 on the opposite side (a +X side) from the one end portion 11e in the X direction, end portions 12f and 13f of the working electrode 12 and the counter electrode 13, respectively, are set to be a first pair of electrode terminals.

A pair of wires 42 and 43 that are connected to a resistance portion 14, which will be described later, are provided between the working electrode 12 and the counter electrode 13 on the surface 11a of the substrate 11 so as to be distanced from each other and extend in narrow band shapes along the X direction. Like the working electrode 12 and the counter electrode 13, the wires 42 and 43 are formed by screen-printing a conductive carbon paste or the like. In a region toward the end portion 11f of the substrate 11 in the X direction (a +X side), end portions 42f and 43f of the wires 42 and 43, respectively, are set to be a second pair of electrode terminals.

The electrode terminals 12f, 13f, 42f, and 43f are expected to make contact with respective contact points 62, 63, 64, and 65 provided in the main body 50 and mentioned later, when the test strip 10 is mounted in the main body 50.

End portions (the short sides of the L shape) 12e and 13e of the working electrode 12 and the counter electrode 13, respectively, are distanced from each other in the X direction. A sensor unit 15, constituted by a circular reagent layer in this example, is provided spanning a space between the end portions 12e and 13e of the working electrode 12 and the counter electrode 13.

The sensor unit 15 is formed as a solid entity in which an oxidoreductase is dispersed throughout a mediator (an electron transfer substance). An iron complex such as potassium ferricyanide, an Ru complex that takes $NH_3$ as a ligand, or the like is used as the electron transfer substance. The oxidoreductase is selected based on the type of the specific component to be measured. For example, in the case where blood sugar (glucose) is to be measured, glucose dehydrogenase, glucose oxidase, or the like is used as the oxidoreductase. In the case where cholesterol is to be measured, cholesterol dehydrogenase, cholesterol oxidase, or the like is used as the oxidoreductase. In the case where lactic acid is to be measured, lactate dehydrogenase, lactate oxidase, or the like is used as the oxidoreductase.

This example assumes that the sensor unit 15 is formed by dispersing glucose dehydrogenase or glucose oxidase throughout an iron complex or an Ru complex in order to measure blood sugar (glucose).

The resistance portion 14 is provided in approximately the center of the substrate 11 in the X direction and the Y direction. The resistance portion 14 has an electrical resistance Rc expressing attribute information, including a sensitivity, of the test strip 10. Here, "attribute information" can include information expressing the sensitivity of the test strip 10, information for selecting a calibration curve that matches the component to be measured, and the like, for example. In this example, it is assumed that the electrical resistance Re of the resistance portion 14 is set to be variable across 16 stages.

Figure 13:
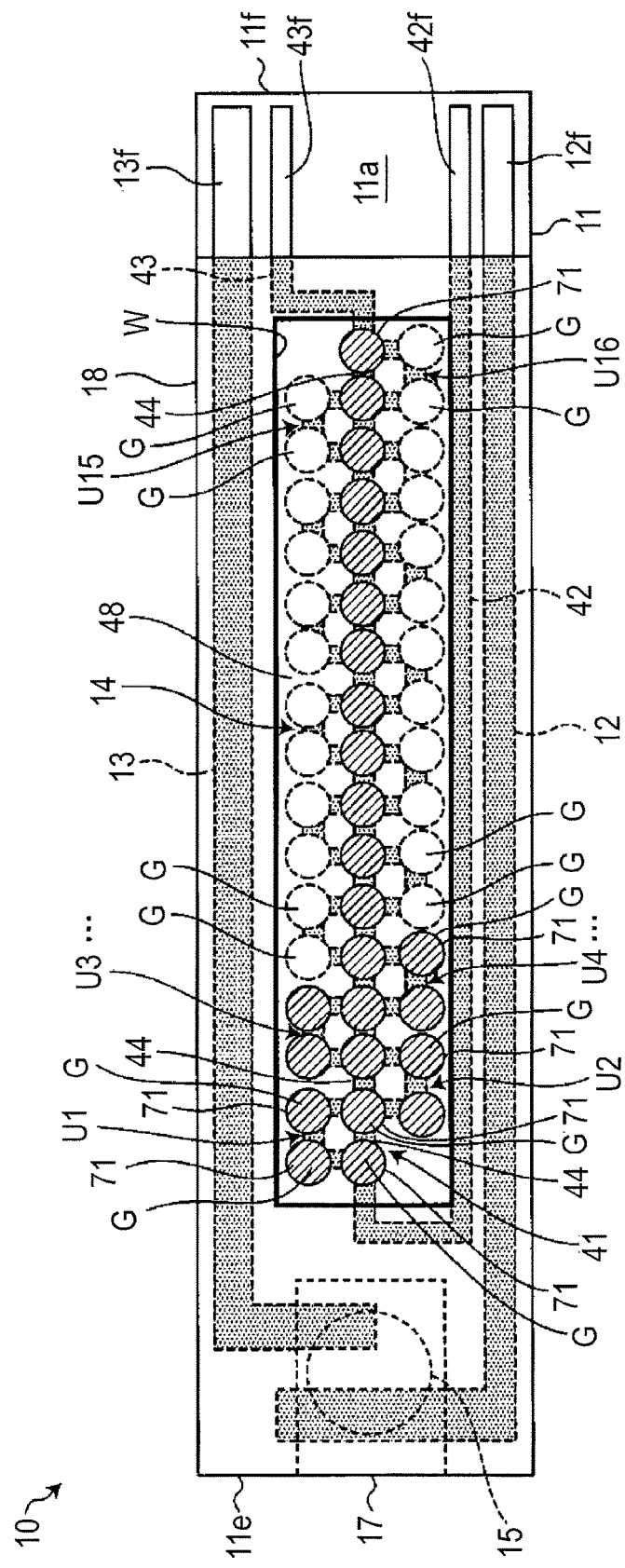
FIG. 13 is a plan view schematically illustrating the stated test strip in a completed state.

Typically, as indicated schematically in the plan view shown in FIG. 13, the resistance portion 14 is constituted by a plurality of narrow patterns 44, 44, and so on that each have a given resistivity and are provided distanced from each other, and substantially circular circular patterns (indicated by hatching) 71, 71, and so on that are provided so as to overlap with respective end portions where the narrow patterns approach each other and that cause those respective end portions to conduct. Note that in FIG. 13, the circles that are hatched indicate that a circular pattern 71 is provided at a grid point G that corresponds to that location, whereas white circles indicated by broken lines indicate that a circular pattern 71 is not provided at a grid point G that corresponds to that location (the same applies in FIG. 16, which will be mentioned later).

As indicated in FIG. 2, the resist layer 48, serving as an insulating layer, is further provided on the substrate 11 in regions aside from a region occupied by the sensor unit 15 and regions occupied by the electrode terminals 12f, 13f, 42f, and 43f. The resist layer 48 is formed by screen-printing a light-curable or thermally-curable insulative resist material or the like. The resist layer 48 has a plurality of through-holes 49, 49, and so on in a region corresponding to the resistance portion 14, the through-holes 49 passing through the resist layer in a thickness direction thereof and being arranged in three rows.

An outer shape of the resist layer 48 in an XY plane matches an outer shape of the spacer 16, which will be described later, in the XY plane. In other words, positions of sides 48e, 48f, 48a, 48b, and 48c that form the outer shape of the resist layer 48 in the XY plane match positions of end portions 16e and 16f and side walls 16a, 16b, and 16c of the spacer 16 in the XY plane. A thickness of the resist layer 48 is set to be less than a thickness of the spacer 16.

The approximately plate-shaped spacer 16 and the cover sheet 18 serving as a flat cover are further affixed in that order upon the substrate 11.

The spacer 16 and the cover sheet 18 are both configured of an insulative plastic material, and have overall narrow rectangular shapes that extend in the X direction. The dimensions of the spacer 16 and the cover sheet 18 in a Y direction match the dimension of the substrate 11 in the Y direction. The dimensions of the spacer 16 and the cover sheet 18 in the X direction are set to be shorter than the dimension of the substrate 11 in the X direction. Specifically, respective end portions 16e and 18e of the spacer 16 and the cover sheet 18 are in the same position as the one end portion 11e of the substrate 11 in a region toward the end portion 11e of the substrate 11 in the X direction (the −X side), but respective end portions 16f and 18f of the spacer 16 and the cover sheet 18 are in positions receded from the other end portion 11f of the substrate 11 in a region toward the other end portion 11f of the substrate 11 on the opposite side from the one end portion 11e in the X direction (the +X side). As a result, the end portions 12f and 13f of the working electrode 12 and the counter electrode 13 and the end portions 42f and 43f of the wires 42 and 43 are exposed as electrode terminals. Accordingly, these electrode terminals 12f, 13f, 42f, and 43f can make contact with the contact points 62, 63, 64, and 65, respectively, of the main body 50, mentioned later, when the test strip 10 is mounted in the main body 50.

The end portion 16e of the spacer 16 on the −X side is recessed like a square with one side open so as to form a channel 17 from the end portion 11e of the substrate 11 to the sensor unit 15. As a result, the spacer 16 includes side walls 16a and 16b that face each other and a side wall 16c that connects the side walls 16a and 16b.

A region in the vicinity of the end portion 18e of the cover sheet 18 on the −X side covers the sensor unit 15 by spanning the side walls 16a and 16b of the spacer 16 that face each other.

Through this, the bodily fluid deposited on the end portion 11e of the substrate 11 on the −X side reaches the sensor unit 15 through the channel 17 through a capillary phenomenon, for example. A layer of the bodily fluid is formed on the sensor unit 15 having a constant thickness based on the height of the spacer 16 (and of the resist layer 48). Accordingly, the amount of the bodily fluid to be measured that makes contact with the sensor unit 15 on the substrate 11 is set, which makes it possible to accurately measure the concentration.

A through-hole for ventilation may be provided in a part, of the cover sheet 18, that is in the vicinity of the side wall 16c facing the channel 17 but that does not directly oppose the sensor unit 15. Through this, air present in the channel 17 escapes through the through-hole when the bodily fluid deposited on the end portion 11e of the substrate 11 on the −X side thereof enters into the channel 17 through the capillary phenomenon. Accordingly, the bodily fluid can enter into the channel 17 with ease.

The spacer 16 and the cover sheet 18 have openings 16w and 18w (collectively called an "opening W") in a region corresponding to the resistance portion 14 on the substrate 11. Through this, all of the grid points G, G, and so on of the resistance portion 14 are exposed on the substrate 11 through the opening W and the plurality of through-holes 49, 49, and so on in the resist layer 48. Accordingly, it is easy to adjust and set the electrical resistance Re of the resistance portion 14 in accordance with the sensitivity of the sensor unit 15 after the spacer 16 and the cover sheet 18 have been provided on the substrate 11 and the electrical characteristics of the test strip 10 have been determined.

Figure 3A:
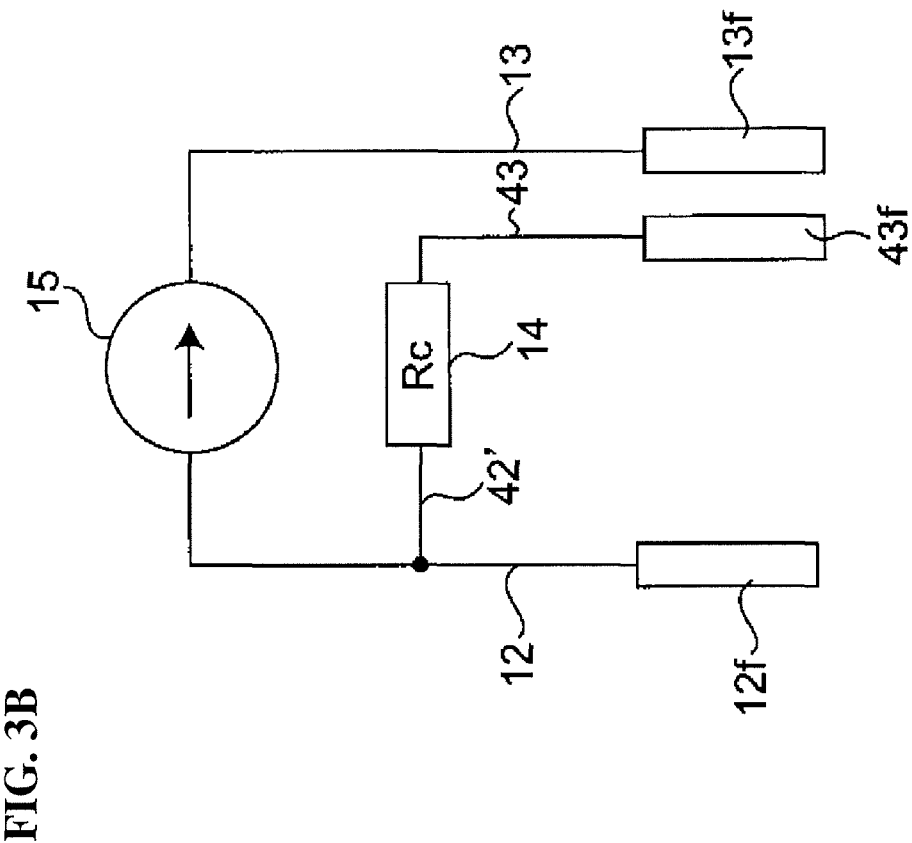
FIG. 3A is a diagram illustrating an equivalent circuit of the stated test strip.

When in a completed state, an equivalent circuit of the test strip 10 is expressed as illustrated in FIG. 3A.

When the bodily fluid (blood) of the measurement subject is not present on the sensor unit 15 of the test strip 10 (this will be called a "bodily fluid undeposited state"), the electrical resistance of the sensor unit 15 is substantially infinite.

On the other hand, when the blood of the measurement subject is deposited on the test strip 10 and makes contact with the sensor unit 15 (this will be called a "bodily fluid deposited state"), the sensor unit 15 acts as a current source and produces an electromotive current, as illustrated in FIG. 3A. The levels illustrated in the following Table 1 can be given as an example of a correspondence relationship between a blood sugar level and the electromotive current in the sensor unit 15.

TABLE 1

| blood sugar level [mg/dL] | electromotive current [nA] |
|---|---|
| 90 | 0.1 |
| 180 | 1.3 |
| 250 | 2.3 |
| 450 | 5.0 |
| 600 | 7.0 |

Table 1 illustrates that, for example, when the blood sugar level is 90 mg/dL, the sensor unit 15 produces a current of 0.1 nA. When the blood sugar level is 180 mg/dL, the sensor unit 15 produces a current of 1.3 nA. When the blood sugar level is 600 mg/dL, the sensor unit 15 produces a current of 7.0 nA.

However, with current mass production techniques, this correspondence relationship between the blood sugar level and the electromotive current of the sensor unit 15 (expressed in this example as a calibration curve) varies, for example, from lot to lot of the manufactured test strips. It is desirable to use a calibration curve based on the sensitivity of the sensor unit 15 in order to accurately calculate the blood sugar level from the electromotive current. It is desirable to refer to the electrical resistance Re of the resistance portion 14 and use a calibration curve based on the sensitivity expressed by that electrical resistance Rc.

Test Strip Manufacturing Method

Figure 8:
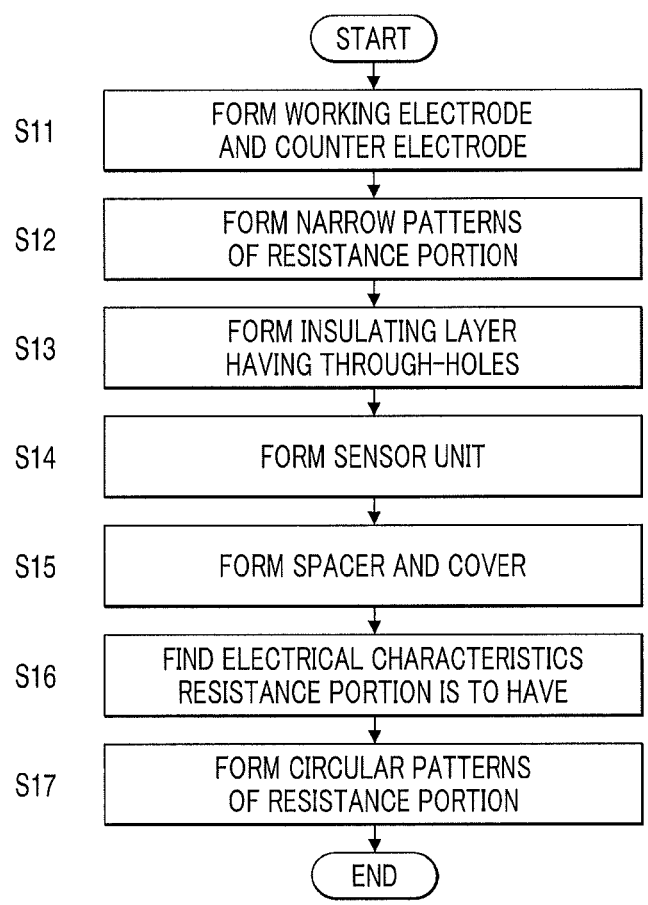
FIG. 8 is a diagram illustrating the flow of a manufacturing method according to an embodiment for manufacturing the stated test strip.
Figure 9:
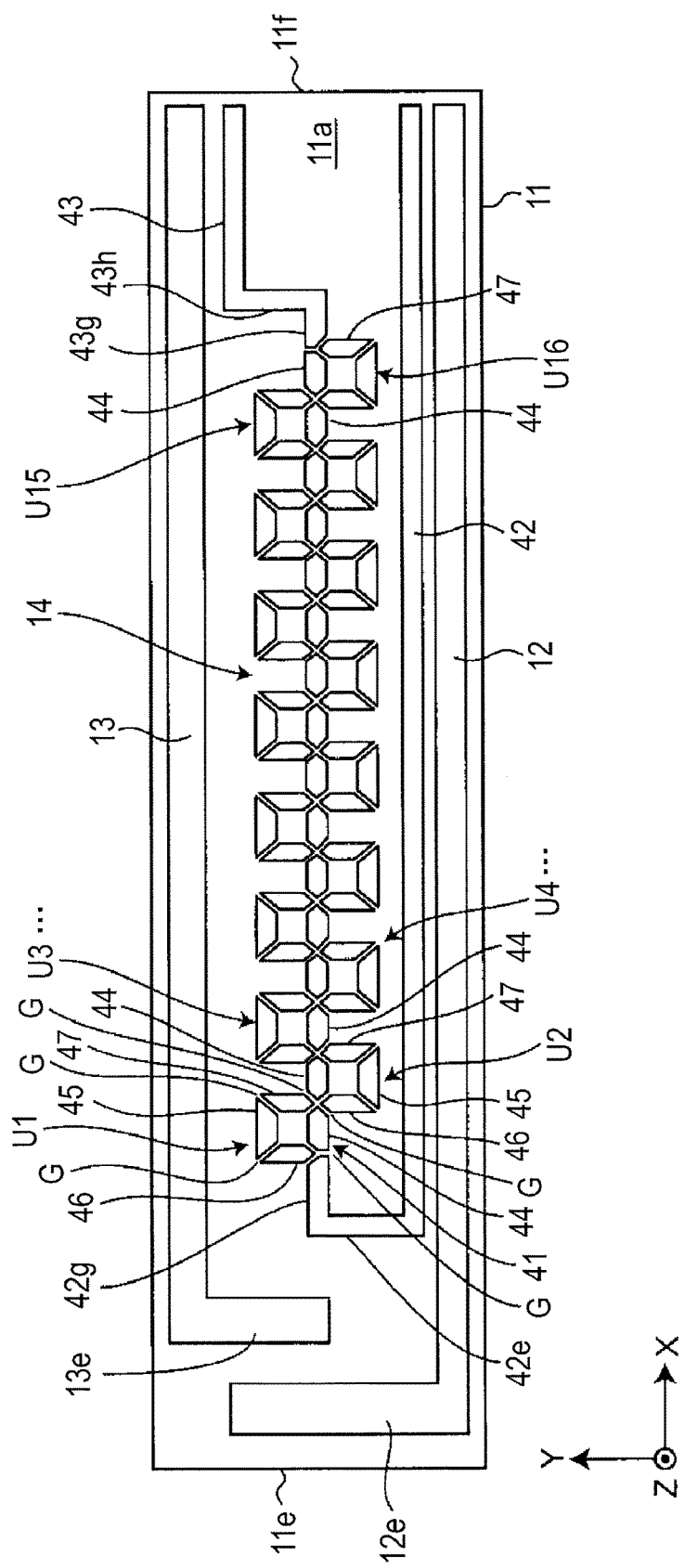
FIG. 9 is a plan view illustrating a state partway through the manufacture of the stated test strip.

FIG. 8 illustrates the flow of a manufacturing method according to an embodiment for manufacturing the test strip 10. The manufacturing method of the test strip 10 will be described based on this flow, with reference to the plan views indicated in FIG. 9 to FIG. 13.

i) First, in step S11 of FIG. 8, the pair of the working electrode 12 and the counter electrode 13 (including the first pair of electrode terminals 12f and 13f) and the pair of the wires 42 and 43 (including the second pair of electrode terminals 42f and 43f) having the configurations described earlier are formed on the surface 11a of the substrate 11 as indicated in FIG. 9 by screen-printing a conductive carbon paste or the like, in this example.

In this example, the wire 42 is provided between the resistance portion 14 and the working electrode 12, extending in a narrow band shape parallel to the working electrode 12 along the X direction. The wire 42 is provided with a portion 42e that is bent in the +Y direction and a portion 42g that is further bent in the +X direction from the portion 42*e* so that the wire 42 can be connected to an end portion on the −X side of the resistance portion 14 that is formed next.

The wire 43 extends in a narrow band shape parallel to the counter electrode 13 along the X direction, in a region near the end portion 11*f* on the −X side of the substrate 11. The wire 43 is provided with a portion 43*h* that is bent in the −Y direction and a portion 43*g* that is further bent in the −X direction from the portion 43*h* so that the wire 43 can be connected to an end portion on the +X side of the resistance portion 14 that is formed next.

ii) Next, in step S12 of FIG. 8, a plurality of narrow patterns 44, 45, 46, and 47 of the resistance portions 14 that each have a given resistivity are formed on the surface 11*a* of the substrate 11 in approximately the center of the substrate 11 relative to the X direction and the Y direction of the substrate 11, as indicated in FIG. 9. In this example, the narrow patterns 44, 45, 46, and 47 are formed, for example, by screen-printing a conductive plastic containing carbon at a thickness of approximately 10 μm to 20 μm and then curing the printed plastic.

The plurality of narrow patterns 44, 45, 46, and 47 are in this example arranged so as to form the respective segments of substantially square grids U1, U2, and so on up to U16. More specifically, the plurality (16, in this example) of narrow patterns 44, 44, and so on are arranged so as to form segments arranged in one row along a longer direction (the X direction) of the substrate 11 (this row is indicated by reference numeral 41). On both sides of the row 41, three each of the narrow patterns 45, 46, and 47 are arranged so as to form unit grids U1, U2, and so on up to U16 that contain respective corresponding segments 44, 44, and so on and that are arranged along the longer direction in an alternating manner.

In this manner, the plurality of narrow patterns 44, 45, 46, and 47 are arranged so as to form the respective segments of the substantially square grids U1, U2, and so on up to U16, and thus the narrow patterns 44, 45, 46, and 47 can be laid out with ease. For example, when manufacturing a printing plate for a screen printing method, it is easy to design the plate.

Figure 18A:
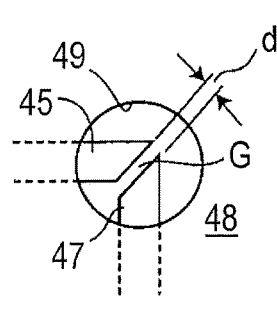
FIGS. 18A, 18B, and 18C are diagrams respectively illustrating states near grid points where end portions of two, three, and four narrow patterns in resistance portions of respective test strips approach each other.
Figure 18B:
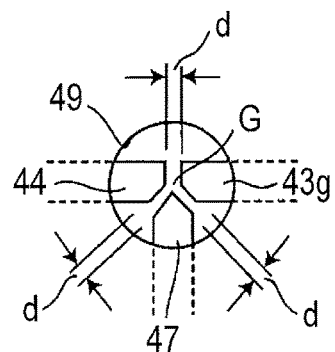
Figure 18C:
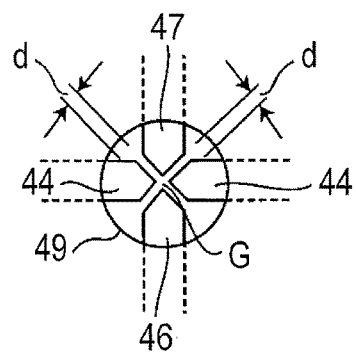

At each grid point G in the unit grids U1, U2, and so on up to U16, a gap d having a constant dimension with respect to a width direction (a direction orthogonal to the longer direction of each narrow pattern) is in this example provided between each end portion where the narrow patterns 44, 45, 46, and 47 are near each other, as can be seen by the enlargements illustrated in FIGS. 18A, 18B, and 18C.

FIG. 18A illustrates a state near an L-shaped grid point G where there are two end portions of narrow patterns (the narrow patterns 45 and 47, in this example) that are near each other, as with an upper-right (in FIG. 9) grid point G of the unit grid U1 in FIG. 9, for example. In this type of L-shaped grid point G, the end portions of each of the narrow patterns 45 and 47 form sides that are angled by 45° relative to the longer direction of the narrow patterns 45 and 47. As a result, the gap d having a constant dimension is provided between the end portions of the narrow patterns 45 and 47.

FIG. 18B illustrates a state near a T-shaped grid point G where an end portion of the wire 43*g* is also near the two end portions of narrow patterns (the narrow patterns 44 and 47, in this example) that are near each other, as with an upper-right (in FIG. 9) grid point G of the unit grid U16 in FIG. 9, for example. In this type of T-shaped grid point G, an end portion of the narrow pattern 47 that corresponds to the trunk of the T has an apex having a 90° pointed shape (formed of two sides that are angled at 45° relative to the longer direction of the narrow pattern 47). The end portion of the narrow pattern 44 and the end portion of the wire 43*g* that are arranged in a row each have mesa shapes (that is, include flat sides that oppose each other and angled sides that continue from the flat sides and are angled by 45°). The angled side of the end portion of the narrow pattern 44 and the angled side of the end portion of the wire 43*g* respectively oppose the corresponding angled side of the end portion of the narrow pattern 47. As a result, the gap d having a constant dimension is provided between the end portion of the narrow pattern 44, the end portion of the narrow pattern 47, and the end portion of the wire 43*g*.

Figure 10:
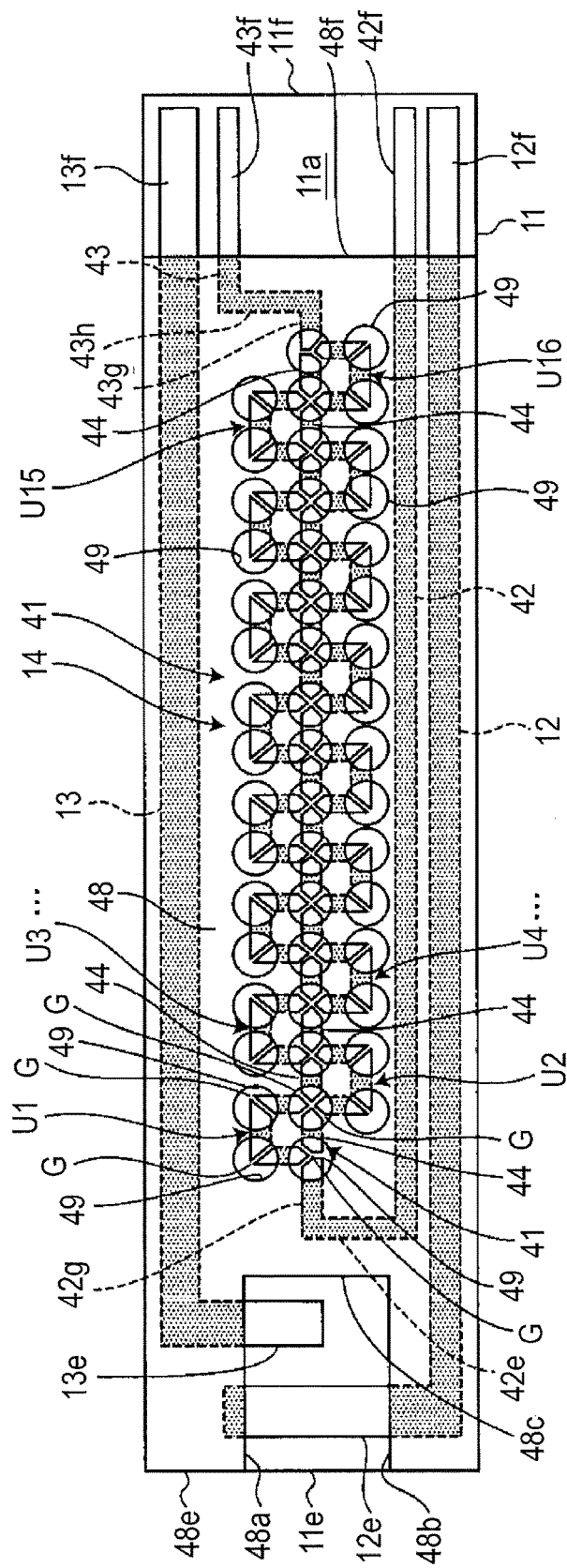
FIG. 10 is a plan view illustrating a state partway through the manufacture of the stated test strip.

FIG. 18C illustrates a state near a +-shaped grid point G where there are four end portions of narrow patterns (the narrow patterns 44, 44, 46, and 47, in this example) that are near each other, as with a lower-right (in FIG. 9) grid point G of the unit grid U1 in FIG. 9, for example. In this type of T-shaped grid point G, the end portion of each of the narrow patterns 44, 44, 46, and 47 has an apex having a 90° pointed shape (formed of two sides that are angled at 45° relative to the longer direction of the narrow patterns 44, 44, 46, and 47). As a result, the gap d having a constant dimension is provided between the end portions of the narrow patterns 44, 44, 46, and 47.

iii) Next, in step S13 of FIG. 8, the resist layer 48 is formed as an insulating layer, as indicated in FIG. 10. In this example, the resist layer 48 is formed at a thickness within a range of 1 μm to 10 μm, for example, and typically at approximately several μm, by screen-printing a light-curable or thermally-curable insulative resist material or the like.

The resist layer 48 has an outer shape in the XY plane as described earlier, and covers most of the working electrode 12, the counter electrode 13, and the wires 42 and 43 as well as active portions of the narrow patterns 44, 45, 46, and 47 aside from the end portions thereof.

Meanwhile, the resist layer 48 has circular through-holes 49 in locations corresponding to each grid point G of the unit grids U1, U2, and so on up to U16. The end portions of the narrow patterns 44, 45, 46, and 47 that are near each other are exposed through the through-holes 49. Note that respective end portions of the wires 42*g* and 43*g* are also exposed at both ends of the overall resistance portion 14, or in other words, at the grid point G on the lower-left (in FIG. 10) of the unit grid U1 and at the grid point G on the upper-right (in FIG. 10) of the unit grid U16.

Figure 20:
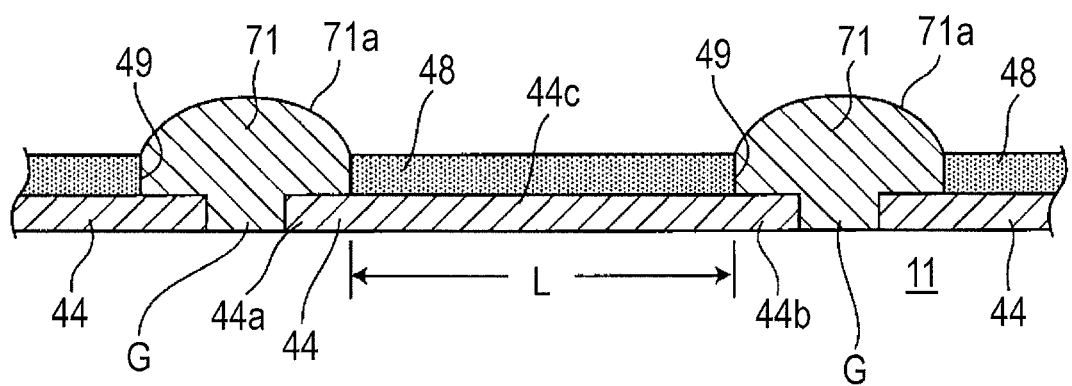
FIG. 20 is a diagram illustrating examples of a cross-section of a circular pattern and an active portion of a narrow pattern in resistance portions of respective test strips.

For example, as illustrated in FIG. 20, in a single narrow pattern 44, an active portion 44*c* aside from end portions 44*a* and 44*b* is covered by the resist layer 48, whereas the end portions 44*a* and 44*b* are exposed through the through-holes 49 at locations corresponding to the grid points G and G. Note that the circular patterns 71, 71, and so on are also illustrated in FIG. 20.

In this manner, the active portions of the narrow patterns 44, 45, 46, and 47 aside from the end portions thereof are covered, and thus the electrical resistance of the active portions of the narrow patterns 44, 45, 46, and 47 contributes to the electrical resistance Rc of the resistance portion 14 as a whole with certainty.

Meanwhile, the plurality of narrow patterns 44, 45, 46, and 47 form the respective segments of square grids. As a result, lengths L and cross-sectional areas (corresponding to a width w×a thickness h) are the same in the active portions of the plurality of narrow patterns 44, 45, 46, and 47 aside from the end portions thereof. Accordingly, the active portions of the plurality of narrow patterns 44, 45, 46, and 47 have the same electrical resistance (indicated by reference numeral Ra; this will be called a unit resistance). Here, assuming that the resistivity (volume resistivity) of each of the narrow patterns 44, 45, 46, and 47 is $\rho=1.0\times10^{-2}$ $\Omega$/cm, the length L=2 mm, the width w=1 mm, and the thickness h=14 µm, the unit resistance of the (active portions of the) narrow patterns 44, 45, 46, and 47 is expressed as:

$$Ra=\rho\times L/(w\times h)\approx 143\text{ k}\Omega$$

The electrical resistance Rc of the resistance portion 14 as a whole is constituted by serial or parallel combinations of the same unit resistances Ra. As a result, in post-processing (step S16), when varying and setting the electrical resistance Rc of the resistance portion 14 so as to express the attribute information of the resistance portion 14 as a whole, the end portions of the narrow patterns 44, 45, 46, and 47 that are near each other (called simply "grid points G" hereinafter) can be selected with ease in order to ensure conduction.

Note that the circular through-holes 49, 49, and so on function to determine borders of the circular patterns 71, 71, and so on in the post-processing (step S16).

Figure 11:
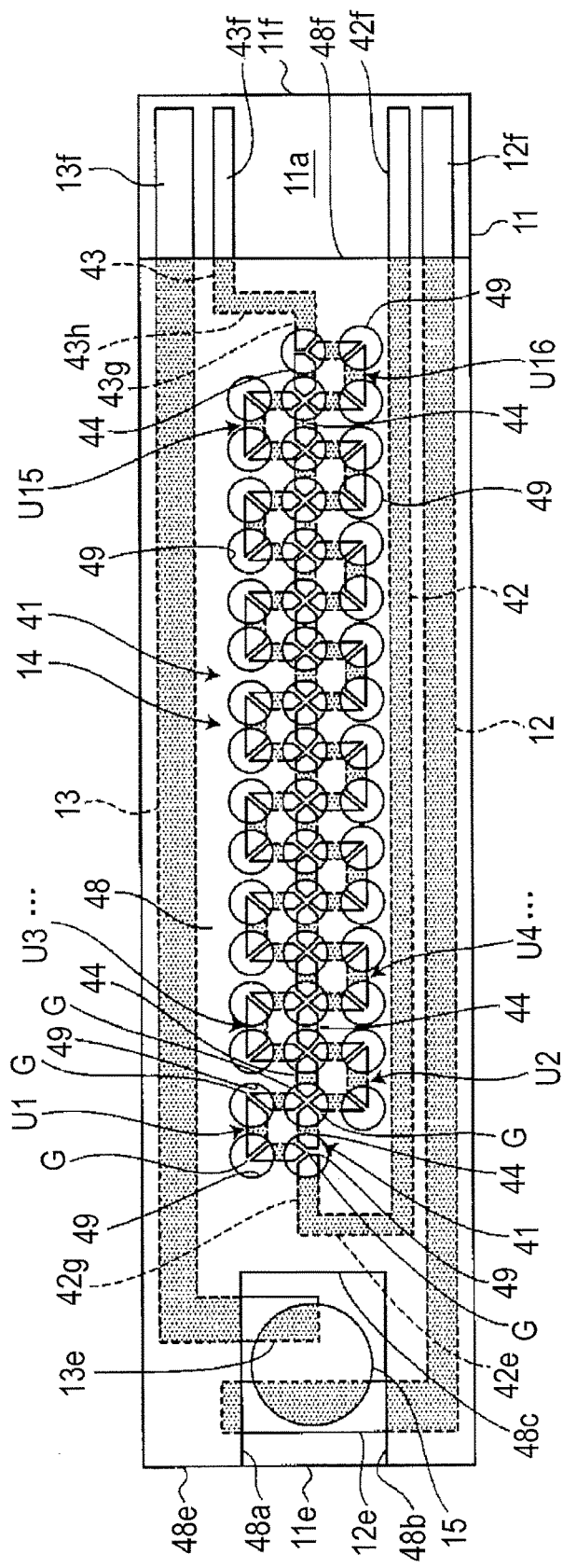
FIG. 11 is a plan view illustrating a state partway through the manufacture of the stated test strip.

Meanwhile, the resist layer 48 is formed before the sensor unit 15 is formed, and thus the process of forming the resist layer 48 does not affect the properties of the sensor unit 15.

iv) Next, in step S14 of FIG. 8, the sensor unit 15 is formed, as indicated in FIG. 11.

In this example, a solid material, formed by dispersing glucose dehydrogenase or glucose oxidase throughout an iron complex or an Ru complex in order to measure blood sugar (glucose), is caused to adhere in a circular shape across the end portions 12e and 13e of the working electrode 12 and the counter electrode 13 as a reagent layer. The sensor unit 15 is formed as a result.

v) Next, in step S15 of FIG. 8, the approximately plate-shaped spacer 16 and the cover sheet 18 serving as a flat cover are further affixed to and provided on the substrate 11 in that order, as indicated in FIG. 2.

As described earlier, the amount of bodily fluid that makes contact with the sensor unit 15 on the substrate 11 is defined by the spacer 16 and the cover sheet 18. Accordingly, the electrical characteristics of the test strip 10 are determined at this stage.

Meanwhile, the end portions on the +X side of the working electrode 12 and the counter electrode 13 are exposed as the first pair of electrode terminals 12f and 13f and the end portions on the +X side of the wires 42 and 43 are exposed as the second pair of electrode terminals 42f and 43f.

Figure 12:
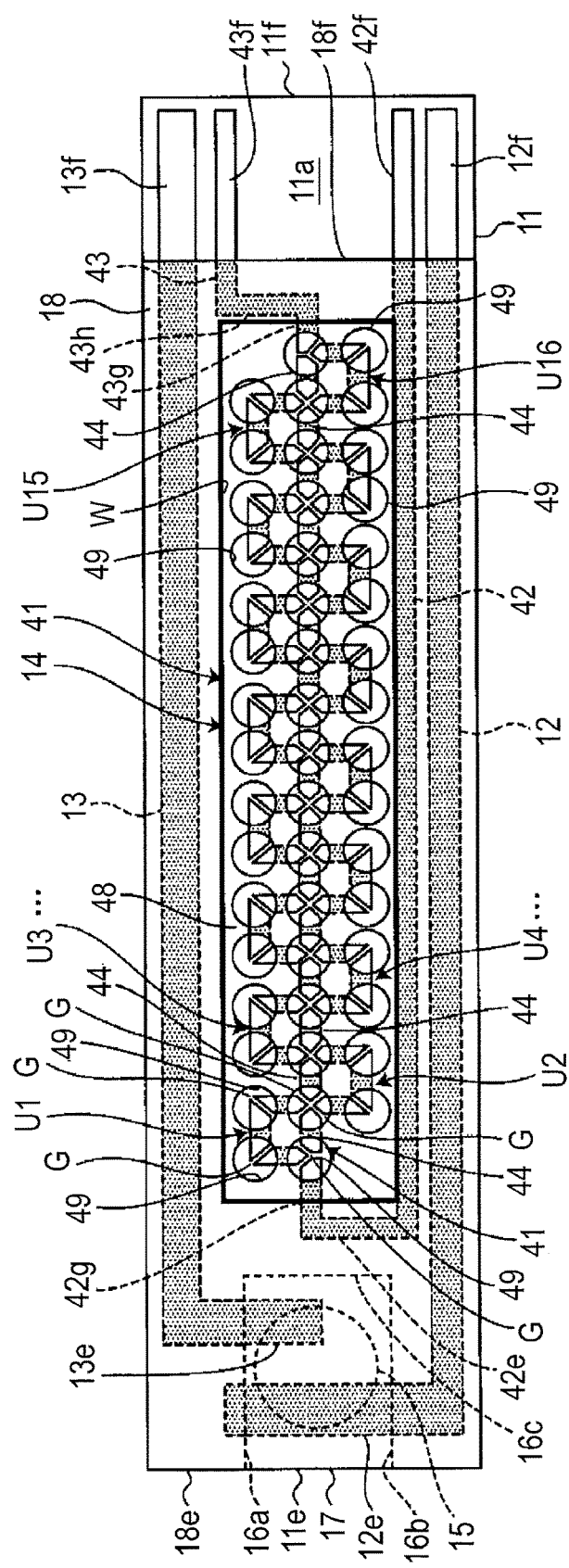
FIG. 12 is a plan view illustrating a state partway through the manufacture of the stated test strip (immediately before potting).

On the other hand, the spacer 16 and the cover sheet 18 have the opening W in a region corresponding to the resistance portion 14 on the substrate 11. Through this, all of the grid points G, G, and so on of the resistance portion 14 are exposed on the substrate 11 through the opening W and the plurality of through-holes 49, 49, and so on in the resist layer 48, as illustrated in FIG. 12. Accordingly, in the post-processing (step S16), it is easy to adjust and set the electrical resistance Rc of the resistance portion 14 in accordance with the sensitivity of the sensor unit 15.

vi) Thereafter, in step S16 of FIG. 8, the electrical resistance Rc that the resistance portion 14 is to have as the attribute information, including the sensitivity of the test strip 10, is found by causing the sensor unit 15 to operate.

Specifically, several test strips (indicated by reference numeral 10M) for monitoring the sensitivity are selected from the same production lot of the test strips 10.

For example, a bodily fluid whose blood sugar level is already known (a sample) is deposited on the sensor units 15 of several test strips 10M, and the electromotive current produced in the sensor unit 15 is observed. For example, bodily fluids having blood sugar levels of 90 [mg/dL] to 600 [mg/dL], as indicated in Table 1, are deposited and the electromotive current [nA] produced in each sensor unit 15 is then observed. A calibration curve expressing a correspondence relationship between the blood sugar level and the electromotive current of the sensor unit 15 is then generated based on the electromotive currents observed in the test strips 10M. It is assumed that the sensitivities of the remaining test strips 10 in that production lot are expressed by this calibration curve.

The calibration curve based on the sensitivity in this manner is then specified based on the value (in 16 stages) of the electrical resistance Rc of the resistance portion 14 during measurement using the test strip 10 (this will be described later).

iv) Next, in step S17 of FIG. 8, the circular patterns 71, 71, and so on of the resistance portion 14 are formed, as indicated in FIG. 13.

Specifically, the grid points G formed by the narrow patterns 44, 45, 46, and 47 so as to have the electrical resistance Rc found for the resistance portion 14 as a whole are selected and the circular patterns 71, 71, and so on are formed so as to overlap with the selected grid points G, G, and so on. The grid points G, G, and so on are made conductive as a result. In the example illustrated in FIG. 13, all of the grid points G arranged in the single row 41 are selected, or the grid points G in the unit grids U1, U2, U3, and U4 on both sides of the single row 41 are selected, and the circular patterns 71, 71, and so on are formed on the selected grid points G.

Note that the circular patterns 71, 71, and so on are also formed at the grid point G on the lower-left (in FIG. 13) of the unit grid U1 and at the grid point G on the upper-right (in FIG. 13) of the unit grid U16. Through this, the resistance portion 14 as a whole is connected to the wires 42 and 43.

The circular patterns 71, 71, and so on are formed by depositing, for example, a conductive plastic, containing a higher concentration of carbon than the conductive plastic used to form the narrow patterns 44, 45, 46, and 47, to serve as a conductive material, through potting at a thickness of 40 µm to 80 µm.

As illustrated in FIG. 20, each of the circular patterns 71, 71, and so on formed through potting has a surface 71a bent in a convex manner in the direction opposite from the substrate 11. Accordingly, the thickness of the circular patterns 71, 71, and so on is easily ensured. Thus if the circular patterns 71, 71, and so on are formed of a typical conductive material, the grid points G, G, and so on that form the narrow patterns 44, 45, 46, and 47 can be substantially shorted. As a result, only the electrical resistance (unit resistance Ra) of the active portions (the portions having the length L) of the narrow patterns 44, 45, 46, and 47 substantially contribute to the electrical resistance Rc of the resistance portion 14 as a whole. The precision of the electrical resistance Rc of the resistance portion 14 as a whole is improved as a result.

In addition, as described above, the borders of the circular patterns 71, 71, and so on are defined by the circular through-holes 49, 49, and so on in the resist layer 48. Accordingly, in step S16, the shapes of the circular patterns 71, 71, and so on can be formed with a high degree of precision.

In addition, the gap d having a constant dimension is provided between the end portions of the narrow patterns 44, 45, 46, and 47, as described earlier with reference to FIG. 18. Accordingly, in step S16, when forming the circular patterns 71, 71, and so on so as to overlap with the grid points G, G, and so on formed by the narrow patterns 44, 45, 46, and 47, the dimensions of the circular patterns 71, 71, and so on (and/or the circular through-holes 49, 49, and so on) can be made comparatively small in accordance with the gap d that has a constant dimension. For example, when forming the circular patterns 71, 71, and so on through potting, a size of a droplet of a conductive material that forms the circular patterns 71, 71, and so on can be set to be comparatively smaller. As a result, the shapes of the circular patterns 71, 71, and so on can be formed with an even higher degree of precision.

The precision of the electrical resistance Rc of the resistance portion 14 as a whole is further improved as a result.

According to this manufacturing method, the plurality of narrow patterns 44, 45, 46, and 47 of the resistance portion 14 can be formed at once in step S12 through screen printing using a single printing plate before the sensor unit 15 is formed, even in the case where the electrical resistance Rc for the resistance portion 14 is set to be variable in order to express the attribute information including the sensitivity of the test strip 10. In other words, it is not necessary to change the printing plate. In addition, the circular patterns 71, 71, and so on in the resistance portion 14 can be formed through potting in step S16 after the sensor unit 15 has been formed and the electrical resistance Rc (attribute information) the resistance portion 14 is to have has been found. At this time, by selecting the grid points G, G, and so on formed by the narrow patterns 44, 45, 46, and 47, the electrical resistance Rc of the resistance portion 14 is set to be variable in order to have the electrical resistance Rc (express the attribute information) found for the resistance portion 14 as a whole.

According to this manufacturing method, expensive equipment is unnecessary, and it is also not necessary to prepare multiple types of printing plates. Accordingly, the cost of manufacture of the test strip 10 can be kept low. In addition, the test strip 10 will not be soiled by debris, and the properties of the sensor unit 15 will not be affected by heat produced during processing after the sensor unit 15 has been formed. Accordingly, the test strip 10 can be manufactured having a high quality.

Variable Setting of Electrical Resistance of Resistance Portion

The electrical resistance Rc of the resistance portion 14 is set to be variable as indicated in FIGS. 14A, 14B, and so on up to 14P. Note that in FIG. 14, grid points G made conductive by circular patterns 71 are indicated by black dots, whereas non-conductive grid points G do not have black dots (the same applied in FIG. 17, mentioned later).

First, as indicated in FIG. 14A, all of the grid points G on segments arranged along the single row 41 are selected and made conductive by the circular patterns 71, 71, and so on in order to obtain a comparatively high resistance value for the resistance portion 14 as a whole. For example, when the number of segments arranged along the single row is expressed as m (m=15 in this example) and the unit resistance of the active portion of each segment in the narrow patterns 44, 45, 46, and 47 is expressed as Ra, the resistance value of the resistance portion 14 as a whole is m×Ra=15 Ra.

If, as indicated in FIG. 14B, a unit grid (U1, for example) on one side of one segment 44 contained in the single row 41 is made conductive, or in other words, if each grid point G at two corner portions distanced from the one segment 44 of the unit grid U1 is made conductive, the contribution of that unit grid U1 will be:

$$\frac{1}{\frac{1}{Ra}+\frac{1}{3Ra}} = \frac{3}{4}Ra$$

Accordingly, the resistance value of the resistance portion 14 will be (¾)Ra+14 Ra=14.75 Ra.

Next, if the unit grid U2 is also made conductive as indicated in FIG. 14C, the contribution of the unit grid U2 will be (¾) Ra. Accordingly, the resistance value of the resistance portion 14 as a whole will be (¾)Ra+(¾)Ra+13 Ra=14.5 Ra.

The number of unit grids made conductive in the resistance portion 14 is sequentially increased in this manner, as indicated in FIGS. 14C to 14P.

In this case, 16 values can be set in a variable manner, in 0.25 Ra steps, for the electrical resistance Rc of the resistance portion 14, from 15 Ra to 11.25 Ra. At this time, it is sufficient to set whether or not the unit grids U1, U2, and so on on one side (or the other side) of the segments contained in the single row 41 are made conductive in order for the resistance portion 14 to express the attribute information as a whole. Accordingly, the grid points G formed by the narrow patterns 44, 45, 46, and 47 are be selected with ease, and the electrical resistance Rc of the resistance portion 14 can be set in a variable manner so that the resistance portion 14 expresses the attribute information as a whole.

Main Body Configuration

As illustrated in FIG. 1, the main body 50 has an approximately rectangular casing 50M that can be held by a user (typically the measurement subject) in one hand. A display unit 55 that functions as a reporting unit and an operating unit 56 through which the user makes operations are provided in a front surface (a top surface, in FIG. 1) of the casing 50M.

A connector portion 61, into which the end portion 11f of the test strip 10 (the substrate 11) is to be inserted as indicated by an arrow A, is provided in an end surface of the casing 50M. When the end portion 11f of the test strip 10 is inserted into the connector portion 61, the electrode terminals 12f and 13f in the working electrode 12 and the counter electrode 13 and the electrode terminals 42f and 43f of the wires 43 and 42 in the test strip 10 make contact and conduct with the respective contact points 62, 63, 64, and 65, which are provided in the connector portion 61. The contact points 62, 63, 64, and 65 are configured as elastic metal plates having approximate boomerang shapes, with an area where the metal plate bends (the apex of the boomerang shape) facing downward so as to make contact with the electrode terminals 12f, 13f, 42f, and 43f of the test strip 10.

Figure 4:
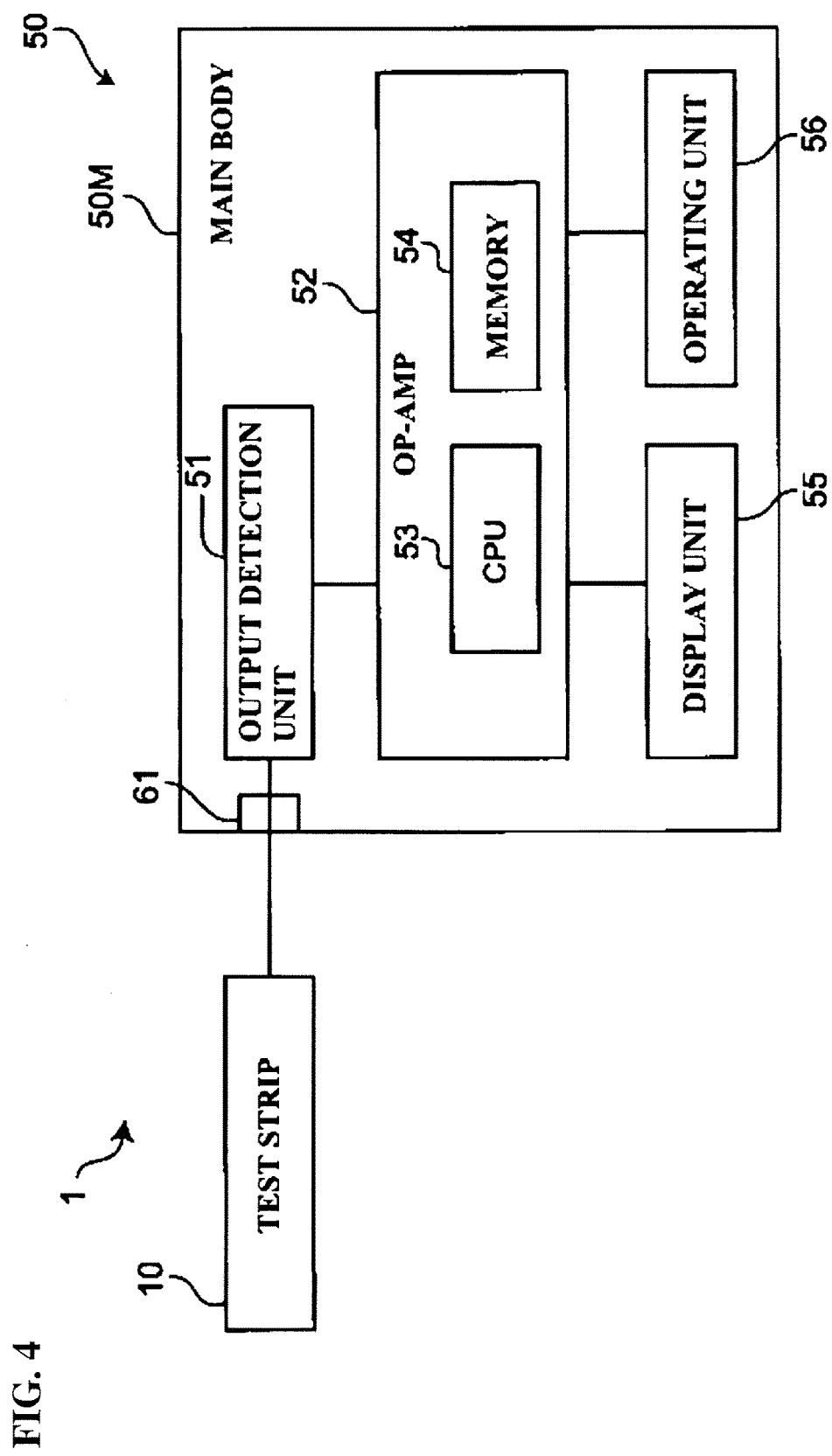
FIG. 4 is a diagram illustrating the functional block configuration of the stated biological component measurement device.

Furthermore, as illustrated in the block diagram of FIG. 4, an output detection unit 51 and a computation unit 52 are provided in the casing 50M of the main body 50.

The output detection unit 51 detects an output from the test strip 10 via the connector portion 61.

The computation unit 52 includes a CPU (Central Processing Unit) 53 serving as a control unit and a memory 54.

The memory 54 stores data of programs for controlling the biological component measurement device 1, calibration curve data expressing the correspondence relationship between the blood sugar level and the electromotive current of the sensor unit 15, measurement result data, and so on. In this example, 16 types of calibration curve data are stored so that variations in the sensitivity of the test strip 10 (the sensor unit 15) (that is, variations in the correspondence relationship between the blood sugar level and the electromotive current of the sensor unit 15) can be accommodated. The memory 54 is also used as a working memory when programs are executed.

The CPU (Central Processing Unit) 53 controls the biological component measurement device 1 in accordance with programs stored in the memory 54. Note that a specific method for control will be described later.

The display unit 55 is configured of a liquid crystal display or an EL (electroluminescent) display in this example. Under the control of the computation unit 52, the display unit 55 displays a measurement result regarding the concentration of a specific component in the bodily fluid (blood sugar level, in this example), as well as other information.

As illustrated in FIG. 1, the operating unit 56 includes three push-button switches 57, 58, and 59. The push-button switch 58 in the center is used to turn the biological component measurement device 1 on and off. The push-button switches 57 and 59 on both sides are used to cycle forward and backward through past measurement results recorded in the memory 54 and display those results in the display unit 55.

Figure 5:
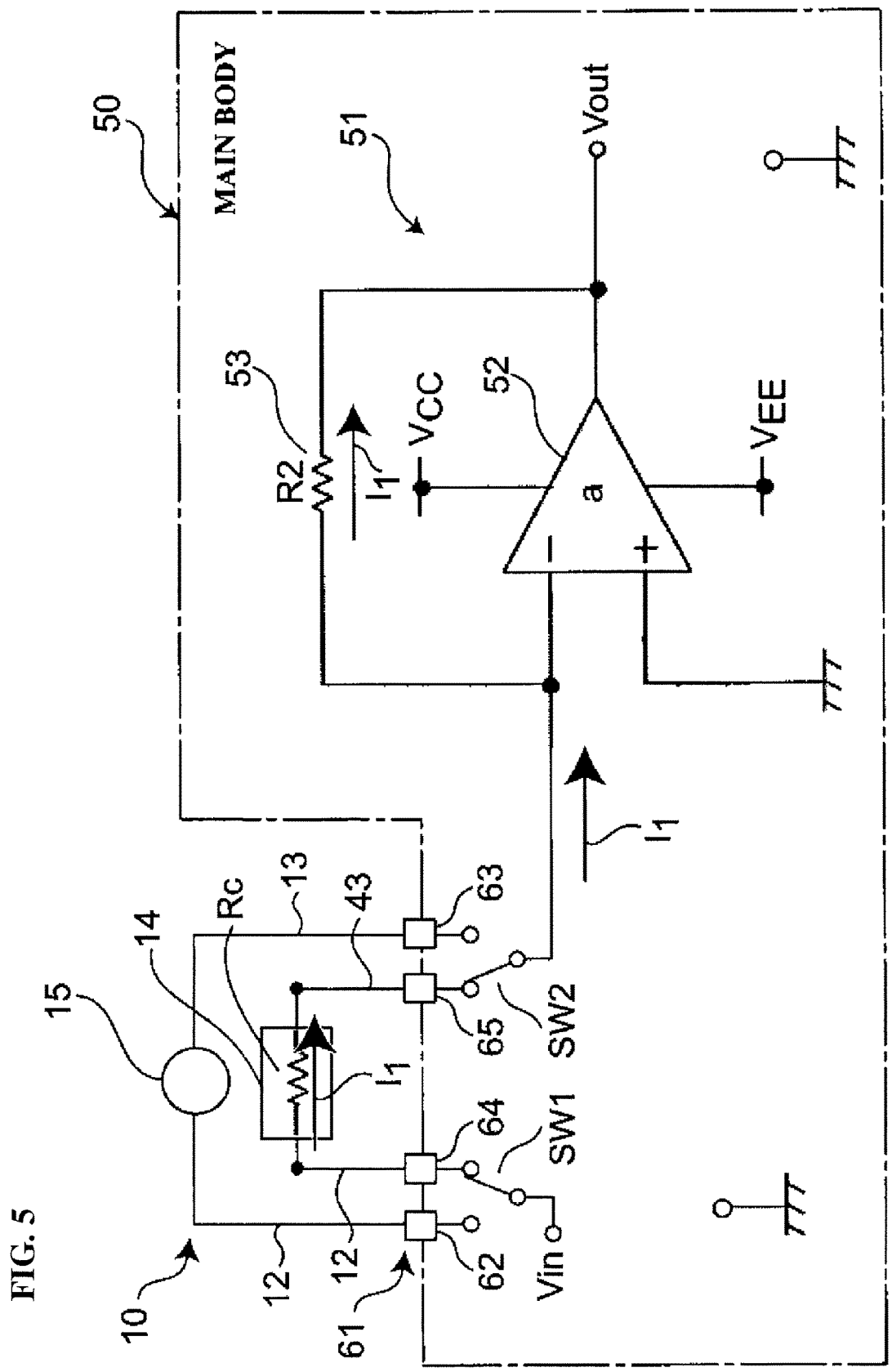
FIG. 5 is a diagram illustrating a scheme for detecting attribute information from the stated test strip, in a bodily fluid undeposited state.

As illustrated in FIG. 5, the output detection unit 51 specifically includes an operational amplifier (called an "op-amp" hereinafter) 52 connected between a source potential $V_{CC}$ and a potential $V_{EE}$ that is lower than the source potential Vcc, a feedback resistance (with a resistance value of R2) 53 connected between an inverting input terminal (−) and an output terminal (a terminal outputting an output voltage Vout) of the op-amp 52, a power source (not illustrated) that applies a predetermined voltage Vin to the resistance portion 14 or the sensor unit 15 of the test strip 10, and switches SW1 and SW2 for switching between a first pair of the contact points 62 and 63 and a second pair of the contact points 64 and 65. An output current from the counter electrode 13 of the test strip 10 is inputted into the inverting input terminal (−) of the op-amp 52 as an output from the test strip 10. A non-inverting input terminal (+) of the op-amp 52 is grounded. Through this configuration, the output detection unit 51 outputs the output voltage Vout based on the output (output current) of the test strip 10.

Assuming the electrical resistance of the test strip 10 is R1, the output voltage of the op-amp 52 is generally expressed as:

$$Vout = -(R2/R1) \times Vin \quad (1)$$

Measurement Method

Figure 7:
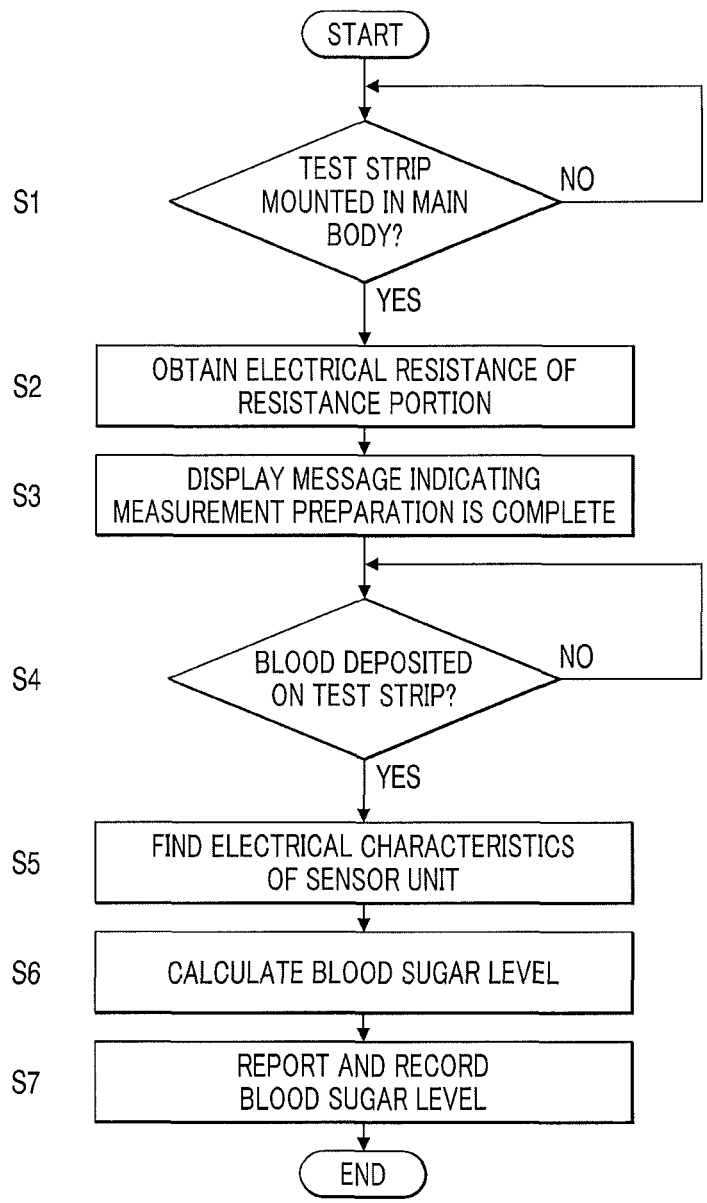
FIG. 7 is a diagram illustrating the flow of a process for measuring a concentration of a specific component in blood, according to the stated biological component measurement device.

Next, a method performed by the biological component measurement device 1 to measure the blood sugar level in blood will be described using the processing flow illustrated in FIG. 7.

i) First, as indicated by step S1 in FIG. 7, the CPU 53 of the main body 50 determines whether or not the test strip 10 has been mounted to the connector portion 61.

In this example, the CPU 53 puts the switches SW1 and SW2 of the output detection unit 51 in a state in which the second pair of the contact points 64 and 65 is selected, as indicated in FIG. 5. In this state, the CPU 53 determines whether or not the test strip 10 has been mounted to the connector portion 61 based on a change in the output voltage Vout of the output detection unit 51 illustrated in FIG. 5. That is, although the output voltage Vout of the output detection unit 51 is substantially zero when the test strip 10 is not mounted, when the test strip 10 is mounted in the bodily fluid undeposited state, R1=Rc (a finite value) as indicated by the aforementioned Formula (1); accordingly, the output voltage Vout of the output detection unit 51 is a value that is substantially not zero, as follows:

$$Vout = -(R2/Rc) \times Vin \quad (2)$$

The CPU 53 determines whether or not the test strip 10 has been mounted in the connector portion 61 based on the change in the output voltage Vout (it is assumed that the values of R2 and Vin and the range of the value of Rc are already known).

Specifically, a range of the value the output voltage Vout is to take is determined according to the aforementioned Formula (2), based on the values of R2 and Vin and the range of the value of Rc. Accordingly, a lower limit value $V_L$ and an upper limit value $V_U$ are set in advance for the value the output voltage Vout is to take. It is determined that the test strip 10 in the bodily fluid undeposited state has been mounted in the case where the output voltage Vout is between the lower limit value $V_L$ and the upper limit value $V_U$ at this stage. It is determined that the test strip 10 is not mounted in the case where the output voltage Vout is below the lower limit value $V_L$. Alternatively, in the case where the output voltage Vout is higher than the upper limit value $V_U$, it is determined that some kind of error has occurred (and in this case, a notification that an error has occurred is displayed in the display unit 55).

Note that instead of or in addition to this, the test strip 10 being mounted may be inputted by the measurement subject pushing the push-button switch 58 of the operating unit 56 (see FIG. 1) at this stage. Through this, the CPU 53 can determine with certainty that the test strip 10 in the bodily fluid undeposited state has been mounted.

ii) Next, it is assumed that the test strip 10 in the bodily fluid undeposited state is mounted in the main body 50. As a result, the electrode terminals 12f and 13f of the working electrode 12 and the counter electrode 13 and the electrode terminals 42f and 43f of the wires 42 and 43 on the substrate 11 (see FIG. 1) respectively make contact with the contact points 62, 63, 64, and 65 provided in the connector portion 61. In this state, as indicated by step S2 in FIG. 7, the CPU 53 obtains the electrical resistance Rc expressing the attribute information from the resistance portion 14 of the test strip 10 through the contact points 64 and 65 and the wires 42 and 43.

Specifically, a current (indicated by $I_1$) flows through the working electrode 12, the resistance portion 14, the counter electrode 13, and the feedback resistance 53 on the substrate 11 in response to the voltage Vin being applied, as illustrated in FIG. 5. In this state, the CPU 53 detects the output voltage Vout of the output detection unit 51 (indicated by Vout1). Through this, the CPU 53 can calculate the electrical resistance Rc expressing the attribute information of the test strip 10 (in this example, the sensitivity of the sensor unit 15, or in other words, the correspondence relationship between the blood sugar level and the electromotive current of the sensor unit 15 as indicated in the examples shown in Table 1), as indicated by the following Formula (3):

$$Rc = -R2 \times (Vin/Vout1) \quad (3)$$

The correspondence relationship between the blood sugar level and the electromotive current of the sensor unit 15, expressed by the electrical resistance Rc, is stored as a calibration curve in the aforementioned memory 54 (see FIG. 4).

iii) When the electrical resistance Rc of the resistance portion 14 has been successfully obtained, the CPU 53 notifies the user that measurement preparation is complete by displaying a notification thereof in the display unit 55, as indicated by step S3 in FIG. 7. For example, "measurement preparation is complete" is displayed. Instead of or in addition to this, "please apply blood to test strip" may be displayed in order to prompt the measurement subject to apply blood to the test strip 10.

iv) Next, the CPU 53 determines whether or not blood has been applied to the test strip 10, as indicated by step S4 in FIG. 7.

Figure 6:
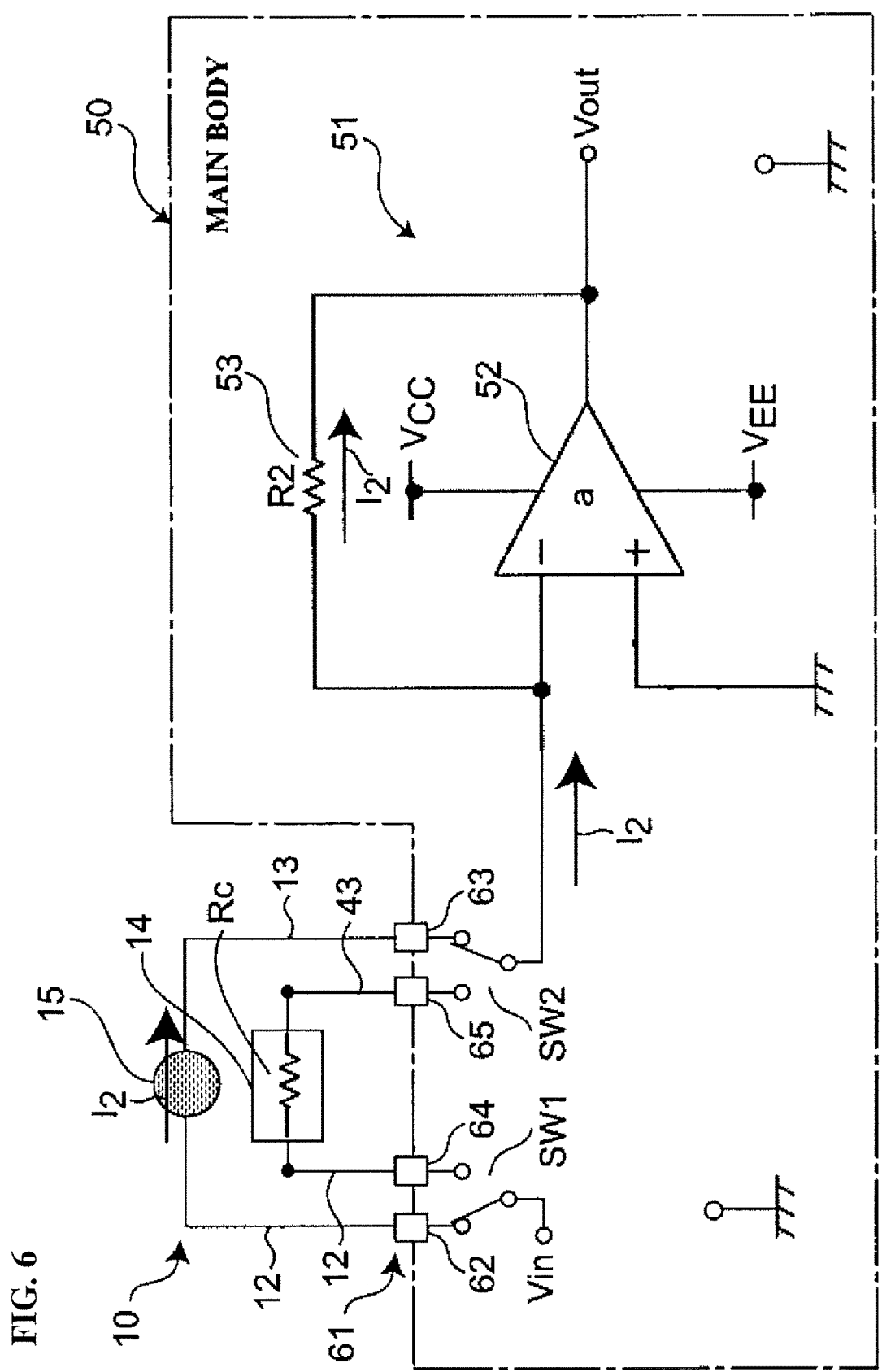
FIG. 6 is a diagram illustrating a scheme for detecting a concentration of a specific component in bodily fluid from the stated test strip, in a bodily fluid deposited state.

In this example, the CPU 53 puts the switches SW1 and SW2 of the output detection unit 51 in a state in which the first pair of the contact points 62 and 63 is selected, as indicated in FIG. 6. In this state, the CPU 53 determines whether or not blood has been applied to the test strip 10 based on a change in the output voltage Vout of the output detection unit 51. In other words, although the output voltage Vout of the output detection unit 51 in the bodily fluid undeposited state is substantially zero, in the bodily fluid deposited state, the sensor unit 15 produces an electrochemical reaction with the blood and produces an electromotive current (indicated by $I_2$) as a change in the electrical characteristics, as illustrated in FIG. 6. In this case, the current $I_2$ flows via the contact points 62 and 63 and the working electrode 12 and the counter electrode 13 on the substrate 11 due to the application of the voltage Vin. In the bodily fluid deposited state, the CPU 53 detects the output voltage Vout of the output detection unit 51 (indicated by Vout2) that is based on the current $I_2$. The CPU 53 determines whether or not blood has been applied to the test strip 10 based on this change in the output voltage Vout from zero to Vout2.

Specifically, it is determined that blood has been applied to the test strip 10 in the case where the output voltage Vout2 is higher than the aforementioned upper limit value $V_U$ at this stage.

Note that instead of or in addition to this, blood being applied to the test strip 10 may be inputted by the measurement subject pushing the push-button switch 58 of the operating unit 56 (see FIG. 1) at this stage. Through this, the CPU 53 can determine with certainty that blood has been applied to the test strip 10.

v) In the bodily fluid deposited state, the CPU 53 finds the electrical characteristics of the sensor unit 15, as indicated by step S5 in FIG. 7.

Specifically, the CPU 53 detects the electromotive current $I_2$ as the electrical characteristics of the sensor unit 15.

vi) Next, as indicated by step S7 in FIG. 7, the CPU 53 calculates the blood sugar level in the blood based on the electromotive current $I_2$ of the sensor unit 15 in the bodily fluid deposited state and the calibration curve (stored in the memory 54) of the test strip 10 expressing the electrical resistance Rc of the resistance portion 14.

vii) Thereafter, as indicated by step S8 in FIG. 7, the CPU 53 notifies the user of the calculated blood sugar level by displaying the blood sugar level in the display unit 55. For example, a display such as "blood sugar level: 180 mg/dL" is made. Along with the display, the CPU 53 stores the blood sugar level in the memory 54. The blood sugar level stored in the memory 54 can be displayed in the display unit 55 by the user (the measurement subject, for example) pressing the push-button switches 57 and 59 of the operating unit 56.

In this manner, according to the biological component measurement device 1, the blood sugar level in the blood of the measurement subject can be measured accurately even in the case where the sensitivity varies from test strip 10 to test strip 10 (and in particular, from sensor unit 15 to sensor unit 15).

Several Variations on Test Strip

Figure 15:
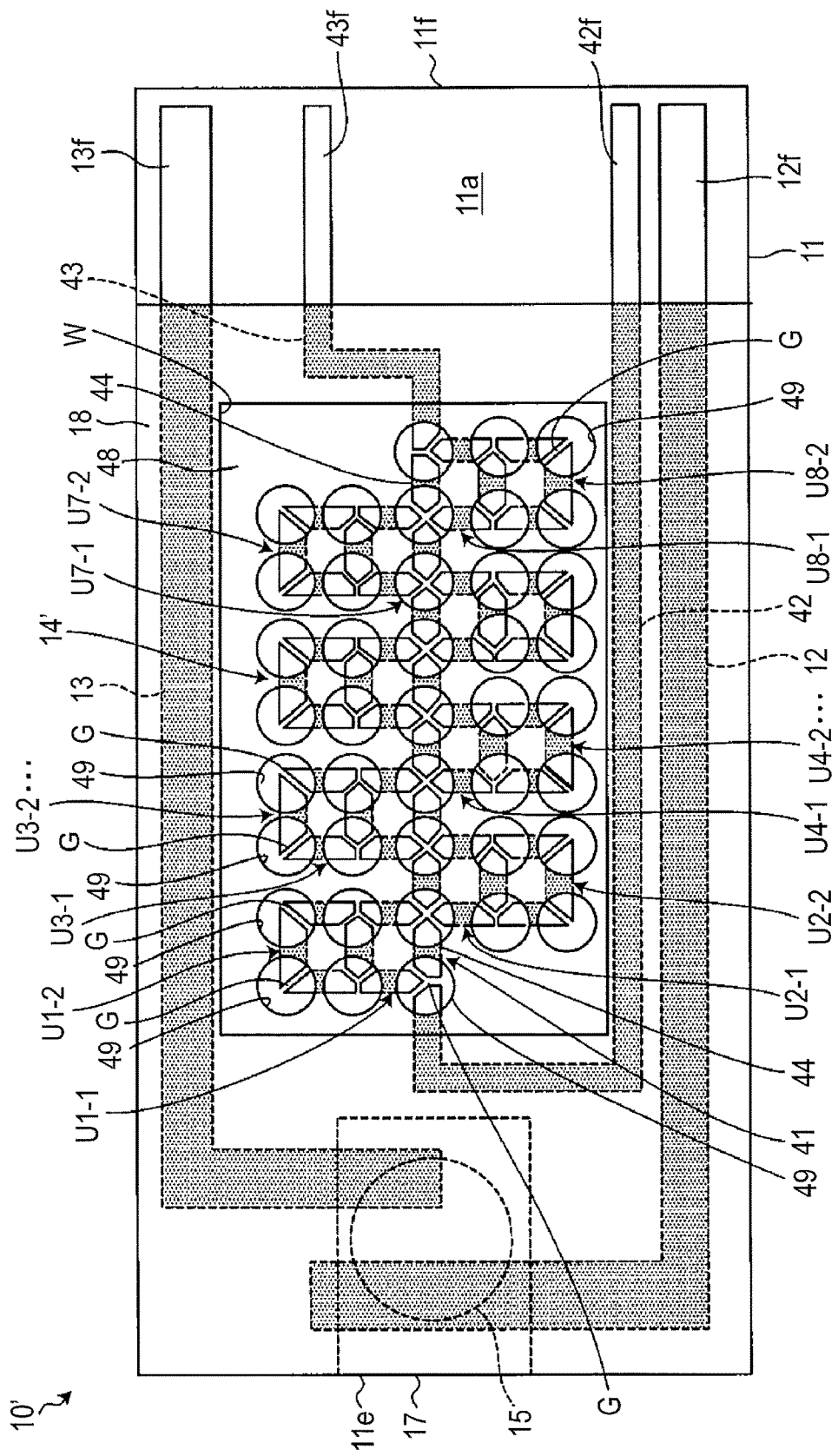
FIG. 15 is a plan view illustrating a state partway through the manufacture of the stated test strip (immediately before potting) according to a variation in which a layout of the resistance portion has been altered.

FIG. 15 illustrates a state partway through the manufacture of the stated test strip (immediately before potting) according to a variation in which a layout of the resistance portion 14 of the test strip 10 described above has been altered.

In a test strip 10' according to this variation, the arrangement of the plurality of narrow patterns in the resistance portion (indicated by reference numeral 14') differs from that in the resistance portion 14 of the test strip 10 described above (see FIG. 12) in that another unit grid is provided in contact with the side opposite from the respective segments arranged in the aforementioned single row 41 of the unit grid.

In other words, in the resistance portion 14' of the test strip 10', a plurality (8, in this example) of narrow patterns 44, 44, and so on are arranged so as to form segments arranged in one row along a longer direction of the substrate 11 (this row is indicated by reference numeral 41). On both sides of the row 41, three each of the narrow patterns are arranged so as to form a set of unit grids U1-1, U2-1, and so on up to U8-1 that contain respective corresponding segments 44, 44, and so on and that are arranged along the longer direction in an alternating manner. Furthermore, three each of the narrow patterns are arranged so as to form another set of unit grids U1-2, U2-2, and so on up to U8-2 on the opposite side of the row 41 from the aforementioned unit grids U1-1, U2-1, and so on up to U8-1.

According to the resistance portion 14' of the test strip 10', the plurality of narrow patterns are arranged so as to form the respective segments of the substantially square grids U1-1 and U1-2, U2-1 and U2-2, and so on up to U8-1 and U8-2, and thus the narrow patterns can be laid out with ease, in the same manner as with the resistance portion 14 of the test strip 10 described above. For example, when manufacturing a printing plate for a screen printing method, it is easy to design the plate.

Figure 16:
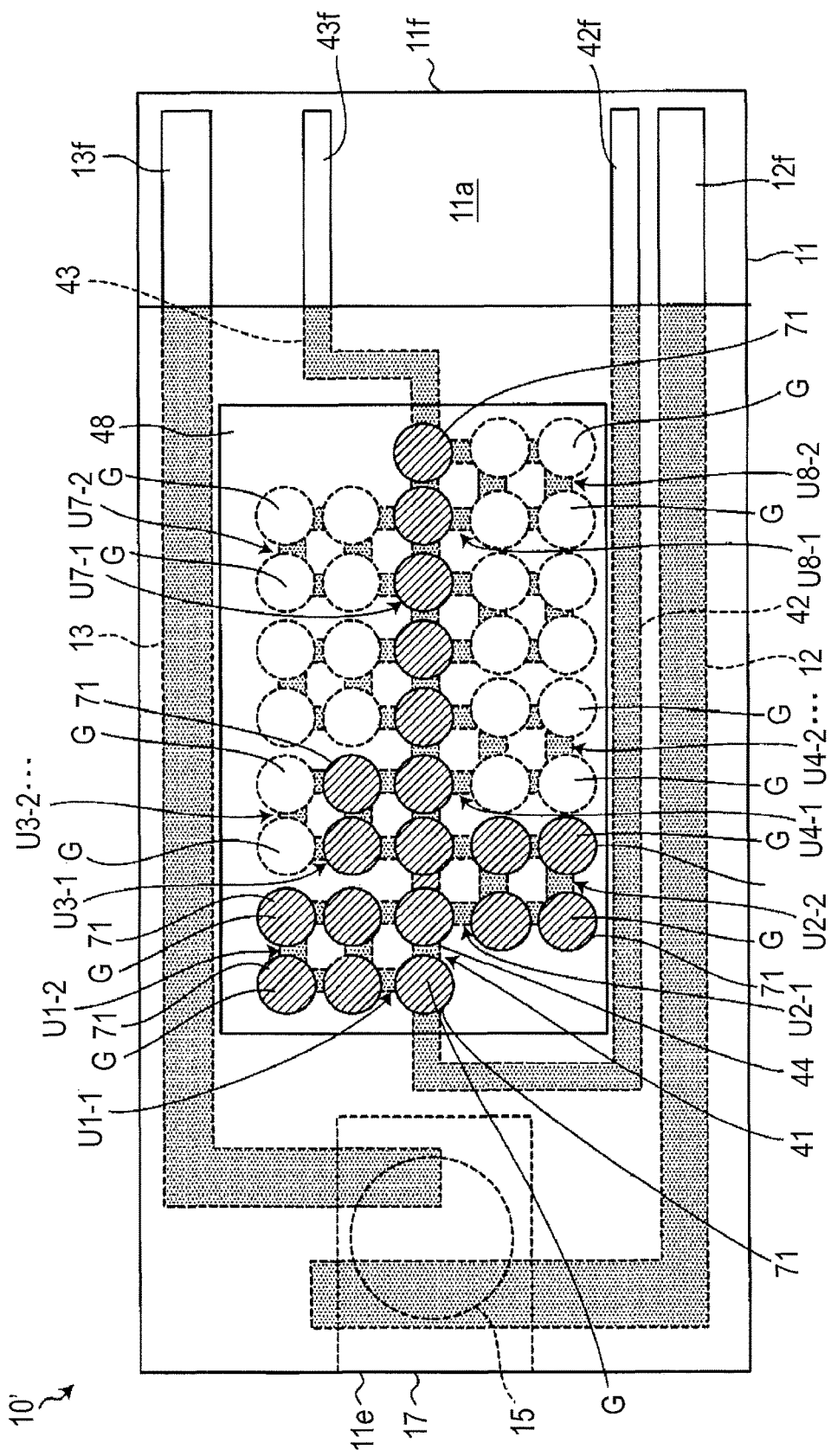
FIG. 16 is a plan view schematically illustrating the test strip illustrated in FIG. 15 in a completed state.

As illustrated in FIG. 16, the circular patterns 71, 71, and so on in the resistance portion 14' are formed through potting in the same manner as with the resistance portion 14 of the test strip 10 described above.

The electrical resistance Rc of the resistance portion 14' is set to be variable as indicated in FIGS. 17A, 17B, and so on up to 17P.

First, as indicated in FIG. 17A, all of the grid points G on segments arranged along the single row 41 are selected and made conductive by the circular patterns 71, 71, and so on in order to obtain a comparatively high resistance value for the resistance portion 14' as a whole. For example, when the number of segments arranged along the single row is expressed as m (m=8 in this example) and the unit resistance of the active portion of each segment in the narrow patterns 44, 45, 46, and 47 is expressed as Ra, the resistance value of the resistance portion 14' as a whole is 8 Ra.

If, as indicated in FIG. 17B, a unit grid (U1-1, for example) on one side of one segment 44 contained in the single row 41 is made conductive, or in other words, if each grid point G at two corner portions distanced from the one segment 44 of the unit grid U1 is made conductive, the contribution of that unit grid U1-1 will be (¾) Ra. Accordingly, the resistance value of the resistance portion 14' as a whole will be (¾)Ra+7 Ra≈7.75 Ra.

Next, if the unit grid U1-2 is also made conductive as indicated in FIG. 17C, the contribution of the unit grids U1-1 and U1-2 will be (11/15) Ra. Accordingly, the resistance value of the resistance portion 14' as a whole will be (11/15)Ra+7 Ra≈7.733 Ra.

Next, if the unit grid U2-1 is also made conductive as indicated in FIG. 17D, the contribution of the unit grid U2-1 will be (¾) Ra. Accordingly, the resistance value of the resistance portion 14' as a whole will be $(^{11}/_{15})Ra+(^{3}/_{4})Ra+6\ Ra\approx 7.483\ Ra$.

Next, if the unit grid U2-2 is also made conductive as indicated in FIG. 17E, the contribution of the unit grids U2-1 and U2-2 will be $(^{11}/_{15})$ Ra. Accordingly, the resistance value of the resistance portion 14' as a whole will be $(^{11}/_{15})Ra+ (^{11}/_{15})Ra+6\ Ra\approx 7.467\ Ra$.

The number of unit grids made conductive in the resistance portion 14' is sequentially increased in this manner, as indicated in FIGS. 17F to 17P.

According to the resistance portion 14', when the number of segments arranged in the single row is expressed as m, (2m+1) values can be set so as to be variable in stages. In other words, the number of variations that can be made on the electrical resistance Rc of the resistance portion 14' is greater than in the case where one unit grid is arranged on each side of the single row. Accordingly, a variety of attribute information can be expressed by the electrical resistance Rc of the resistance portion 14'. Conversely, if the number of variations on the electrical resistance Rc of the resistance portion 14' that is to be set is considered, the number m of segments arranged in the single row 41 can be reduced as compared to the case where one unit grid is arranged on each side of the single row. This means that a dimension of the region of the substrate 11 occupied by the resistance portion 14' can be reduced in the direction of the single row 41 (the X direction). Accordingly, the resistance portion 14' can be laid out with more freedom on the substrate 11.

Note that the arrangement of the plurality of narrow patterns that form the square grids is not limited to those indicated by the resistance portions 14 and 14'. The arrangement of the plurality of narrow patterns that form the square grids may have a shape in which three rows and two columns form a shape similar to a digital "8", a shape in which three rows and three columns form a shape similar to that of a foursquare court, or shapes having a plurality of segments forming four or more rows and columns each, for example.

Figure 19A:
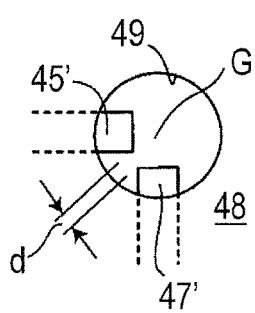
FIGS. 19A, 19B, and 19C are diagrams respectively illustrating other states near grid points where end portions of two, three, and four narrow patterns in resistance portions of respective test strips approach each other.
Figure 19B:
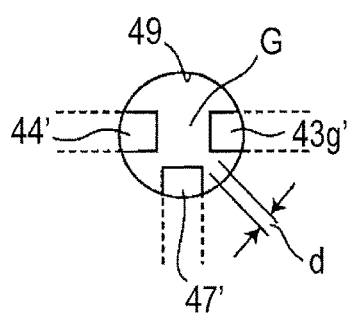
Figure 19C:
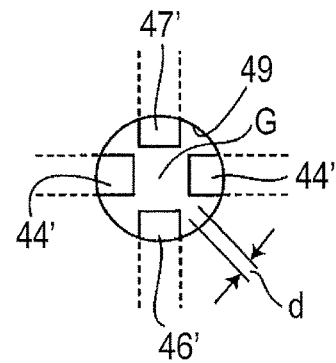

FIGS. 19A, 19B, and 19C illustrate variations on the shapes near the grid points where the end portions of the two, three, and four narrow patterns are near each other in the resistance portion 14 of the test strip 10 illustrated in FIGS. 18A, 18B, and 18C.

In the examples illustrated in FIGS. 19A, 19B, and 19C, at the corresponding L-shaped grid point G, the T-shaped grid point G, and the +-shaped grid point G in FIGS. 18A, 18B, and 18C, the end portions where the narrow patterns are near each other each forms a side that is cut perpendicular relative to the longer direction of the corresponding narrow pattern.

For example, in FIG. 19A, the end portions of narrow patterns 45' and 47' each forms a side that is cut perpendicular to the respective longer directions thereof. As a result, the gap d is provided between the end portions of the narrow patterns 45' and 47' at the area where the end portions are closest to each other.

In FIG. 19B, in addition to the end portions where narrow patterns 44' and 47' are near each other, the end portion of a wire 43g' forms a side that is cut perpendicular to the longer direction thereof. As a result, the gap d is provided between the end portions of the narrow patterns 44' and 47' and between the end portion of the narrow pattern 47' and the end portion of the wire 43g', at the area where the end portions are closest to each other.

In FIG. 19C, the end portions of narrow patterns 44', 44', 46', and 47' each forms a side that is cut perpendicular to the respective longer directions thereof. As a result, the gap d is provided between the end portions of the narrow patterns 44', 44', 46', and 47' at the area where the end portions are closest to each other.

According to the examples illustrated in FIGS. 19A, 19B, and 19C, the narrow patterns 44', 45', 46', and 47' can be laid out with ease. For example, when manufacturing a printing plate for a screen printing method, it is easy to design the plate.

Figure 21:
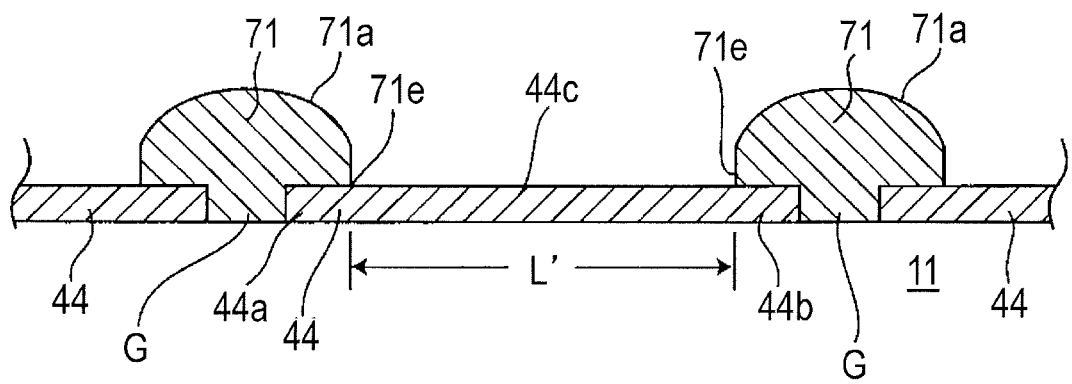
FIG. 21 is a diagram illustrating examples of a cross-section of a circular pattern and an active portion of a narrow pattern in resistance portions of respective test strips, as seen when an insulating layer has been omitted.

Meanwhile, although the resist layer 48 is provided as an insulating layer so as to cover the active portions of the narrow patterns 44, 45, 46, and 47 in the resistance portion 14 in the foregoing examples, the invention is not limited thereto. For example, the resist layer 48 serving as an insulating layer may be omitted, as illustrated in FIG. 21. In this case, a length L' of the active portions of the narrow patterns (the active portion 44c of the narrow pattern 44 is indicated in the example illustrated in FIG. 21) determined substantially by a distance between end portions 71e and 71e of the circular patterns 71 and 71 provided at both ends of the narrow patterns. In this case, the cost of manufacture of the test strip 10 can be kept even lower.

Furthermore, although the foregoing example describes the circular patterns 71 as being formed in the resistance portion 14 through potting, the invention is not limited thereto. For example, the circular patterns 71 of the resistance portion 14 may be formed by affixing circular conductive sheets to the grid points G. In particular, the technique of affixing circular conductive sheets makes it easy to avoid variations in the shapes of the circular patterns 71 when omitting the resist layer 48 that serves as the insulating layer, and is therefore advantageous.

Figure 3B:
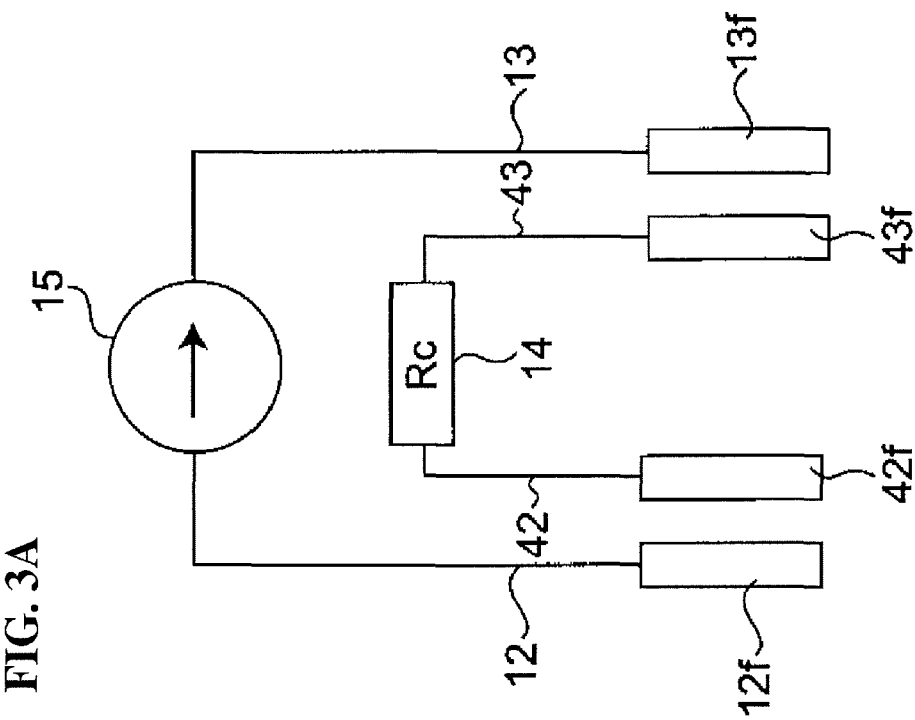
FIG. 3B is a diagram illustrating an equivalent circuit according to a variation on the stated test strip.

Furthermore, although the foregoing example describes the first pair of electrode terminals 12f and 13f and the second pair of electrode terminals 42f and 43f as being provided separately on the substrate 11, the invention is not limited thereto. For example, one electrode 12f in the first pair of electrode terminals and one electrode 42f in the second pair of electrode terminals may be formed in common, as indicated in FIG. 3B. As a result, in the example illustrated in FIG. 3B, the electrode terminal 42f is omitted and the a wire connected to the resistance portion 14 (indicated by reference numeral 42') is connected directly to the working electrode 12. As shown in FIG. 9, for example, the wire 42' corresponds to extending the wire portion 42e in the −Y direction and directly coupling that portion with the working electrode 12. In such a case, according to the test strip 10, it is sufficient for the electrode terminals 12f and 13f of the working electrode 12 and the counter electrode 13 and the electrode terminal 43f of the wire to be disposed on the side of the substrate 11 where the other end portion 11f is located. Accordingly, a large part of the wire 42 can be omitted (with the exception of the portions 42e and 42g on the −X side thereof), and the number of electrode terminals in the test strip 10 can be reduced to 3. Furthermore, the bent portions 43g and 43h of the wire 43 can be omitted and the wire 43 can be formed straight. As such, the test strip 10 can be formed having a smaller size and at a lower cost.

Reducing the number of electrode terminals in the test strip 10 to three makes it possible to reduce the number of contact points in the connector portion 61 to three in the main body 50 side as well. This in turn makes it possible to relax a requirement for dimensional precision when disposing the electrode terminals 12f and 13f of the test strip 10 and the contact points 62 and 63 of the connector portion 61. In addition, in the main body 50, the contact point 62 can be directly coupled with the power source Vin and the switch SW1 (see FIG. 5) can be omitted. As a result, the test strip 10 and the main body 50 can be formed having smaller sizes and at a lower cost.

Although the foregoing example focuses primarily on the case where, for example, blood sugar (glucose) in the blood is measured as the specific component in the bodily fluid, the invention is not limited thereto. The concentration of cholesterol and lactic acid in the blood can also be measured by selecting the reagent layer of the sensor unit 15 from among known materials as appropriate.

In addition, a biological component measurement program stored in the memory 54 may be encoded on a memory or other non-transitory computer-readable recording medium (a memory, a hard disk drive, an optical disk, or the like), and a generic computer may then be caused to execute the aforementioned measurement method.

Furthermore, although the foregoing describes a configuration in which the biological component measurement device 1 is a standalone device, the invention is not limited thereto. The main body 50 may have a communication unit. The communication unit sends information expressing a measurement result (a blood sugar level in the blood, for example) obtained by the CPU 53 to an external device via a network, receives information from an external device via a network and passes the information to the control unit, and so on. Through this, the measurement subject can, for example, receive advice and so on from a doctor over the network. The communication over the network may be wireless or wired.

The aforementioned embodiments are merely examples, and many variations thereon can be carried out without departing from the scope of this invention.

REFERENCE SIGNS LIST

1 biological component measurement device
10, 10' test strip
11 substrate
12 working electrode
13 counter electrode
12f, 13f first pair of electrode terminals
14, 14' resistance portion
42, 43, 42' wire
42f, 43f second pair of electrode terminals
44, 45, 46, 47 narrow pattern
50 main body
55 display unit
61 connector portion
62, 63, 64, 65 contact point
71 circular pattern
G grid point
U1, U2, . . . U16; U1-1, U1-2; U2-1, U2-2; . . . U8-1, U8-2 unit grid

The invention claimed is:

1. A test strip for biological component measurement that is to be mounted in a measurement device main body and on which a bodily fluid of a measurement subject is to be deposited in order to measure a concentration of a specific component in the bodily fluid, the test strip comprising:
a substrate, the substrate including thereon:
a pair of a working electrode and a counter electrode extending in one direction while being distanced from each other;
a sensor unit, formed so as to span a space between the working electrode and the counter electrode toward one end portion in the one direction, configured to produce an electrochemical reaction with the bodily fluid of the measurement subject and produce a change in electrical characteristics;
a resistance portion, formed between both end portions in the one direction and in a region between the working electrode and the counter electrode, having an electrical resistance expressing attribute information including a sensitivity of the test strip;
an insulating layer; and
a pair of wires connected to both ends of the resistance portion,
the pair of the working electrode and the counter electrode and the pair of the wires respectively having a first pair of electrode terminals and a second pair of electrode terminals configured to make contact with contact points provided in the measurement device main body at another end portion on the side opposite from the one end portion in the one direction,
the resistance portion having:
a plurality of narrow patterns, each having a resistivity and provided so as to be distanced from each other, an end portion of each narrow pattern being near an end portion of another narrow pattern; and
predetermined patterns provided so as to overlap locations where the end portions of the narrow patterns are near each other and configured to enable the end portions to conduct with each other,
a substantially plate-shaped spacer and a flat cover further being provided on the substrate,
toward the one end portion in the one direction, the spacer forming side walls that oppose each other on both sides of the sensor unit and the cover covering the sensor unit across the side walls of the spacer that oppose each other so as to define an amount of the bodily fluid that makes contact with the sensor unit on the substrate,
the first pair and second pair of electrode terminals being exposed from the spacer and the cover at the other end portion in the one direction,
the spacer and the cover having an opening that exposes the resistance portion in a region corresponding to the resistance portion between both of the end portions in the one direction, and
wherein each of the predetermined patterns in the resistance portion is formed through potting and has a surface bent in a convex manner in a direction opposite from the substrate, and
the insulating layer configured to cover active portions of the narrow patterns aside from the end portions thereof and includes through-holes that define borders of the predetermined patterns.

2. The test strip according to claim 1, wherein a length and a cross-sectional area of the active portions of the plurality of narrow patterns aside from the end portions thereof are the same.

3. The test strip according to claim 1, wherein one of the terminals in the first pair of electrode terminals and one of the terminals in the second pair of electrode terminals are formed in common.

4. A test strip for biological component measurement that is to be mounted in a measurement device main body and on which a bodily fluid of a measurement subject is to be deposited in order to measure a concentration of a specific component in the bodily fluid, the test strip comprising:

a substrate, the substrate including thereon:
a pair of a working electrode and a counter electrode extending in one direction while being distanced from each other;
a sensor unit, formed so as to span a space between the working electrode and the counter electrode toward one end portion in the one direction, configured to produce an electrochemical reaction with the bodily fluid of the measurement subject and produce a chance in electrical characteristics;
a resistance portion, formed between both end portions in the one direction and in a region between the working electrode and the counter electrode, having an electrical resistance expressing attribute information including a sensitivity of the test strip; and
a pair of wires connected to both ends of the resistance portion,
the pair of the working electrode and the counter electrode and the pair of the wires respectively having a first pair of electrode terminals and a second pair of electrode terminals configured to make contact with contact points provided in the measurement device main body at another end portion on the side opposite from the one end portion in the one direction,
the resistance portion having:
a plurality of narrow patterns, each having a resistivity and provided so as to be distanced from each other, electrically isolated from each other, and electrically isolated from the working electrode and the counter electrode, an end portion of each narrow pattern being near an end portion of another narrow pattern; and
substantially circular patterns provided so as to overlap locations where the end portions of the narrow patterns are near each other and configured to enable the end portions to conduct with each other,
a substantially plate-shaped spacer and a flat cover further being provided on the substrate,
toward the one end portion in the one direction, the spacer forming side walls that oppose each other on both sides of the sensor unit and the cover covering the sensor unit across the side walls of the spacer that oppose each other so as to define an amount of the bodily fluid that makes contact with the sensor unit on the substrate,
the first pair and second pair of electrode terminals being exposed from the spacer and the cover at the other end portion in the one direction,
the spacer and the cover having an opening that exposes the resistance portion in a region corresponding to the resistance portion between both of the end portions in the one direction, and
wherein each of the circular patterns in the resistance portion is formed through potting and has a surface bent in a convex manner in a direction opposite from the substrate,
wherein the plurality of narrow patterns are arranged so as to form respective segments of a substantially square grid; and
at each of grid points in the square grid, a gap is present between respective end portions of the narrow patterns that are near each other.

5. The test strip according to claim 4,
wherein the gap between the respective end portions of the narrow patterns that are near each other is a gap having a constant dimension in a width direction that is orthogonal to a longer direction of the narrow patterns.

6. The test strip according to claim 4,
wherein the arrangement of the plurality of narrow patterns forms a plurality of segments arranged in a single row along a longer direction of the substrate, and forms unit grids, on both sides of the single row, that each contains corresponding segments and that are arranged along the longer direction in an alternating manner; and
both ends of the segments arranged in the single row as a whole are conductive with the pair of wires.

7. The test strip according to claim 6,
wherein the arrangement of the plurality of narrow patterns has other unit grids that make contact with the opposite side of the segments arranged in a single row from the side on which the aforementioned unit grids are located.

8. A test strip for biological component measurement that is to be mounted in a measurement device main body and on which a bodily fluid of a measurement subject is to be deposited in order to measure a concentration of a specific component in the bodily fluid, the test strip comprising:
a substrate, the substrate including thereon:
a pair of a working electrode and a counter electrode extending while being distanced from each other;
a sensor unit, formed so as to span a space between the working electrode and the counter electrode, configured to produce an electrochemical reaction with the bodily fluid of the measurement subject and produce a change in electrical characteristics;
a resistance portion having an electrical resistance expressing attribute information including a sensitivity of the test strip; and
a pair of wires connected to both ends of the resistance portion,
the pair of the working electrode and the counter electrode and the pair of the wires respectively having a first pair of electrode terminals and a second pair of electrode terminals configured to make contact with contact points provided in the measurement device main body, and
the resistance portion having:
a plurality of narrow patterns, each having an resistivity and provided so as to be distanced from each other, an end portion of each narrow pattern being near an end portion of another narrow pattern; and
substantially circular patterns provided so as to overlap locations where the end portions of the narrow patterns are near each other and configured to enable the end portions to conduct with each other, and
the test strip further comprising an insulating layer configured to cover active portions of the narrow patterns aside from the end portions thereof and that includes circular through-holes that define borders of the circular patterns.

9. The test strip according to claim 8,
wherein a spacer that forms side walls that face each other and a flat cover that covers the sensor unit across a space between the side walls of the spacer that face each other are provided on the substrate in order to regulate the amount of the bodily fluid that makes contact with the sensor unit on the substrate; and
the first pair and second pair of electrode terminals and the resistance portion are exposed on the substrate from the spacer and the cover.

10. The test strip according to claim 8,
wherein each of the circular patterns in the resistance portion is formed through potting and has a surface bent in a convex manner in a direction opposite from the substrate.

11. The test strip according to claim 8,
wherein a length and a cross-sectional area of the active portions of the plurality of narrow patterns aside from the end portions thereof are the same.

12. The test strip according to claim 8,
wherein the plurality of narrow patterns are arranged so as to form respective segments of a substantially square grid; and
at each of grid points in the square grid, a gap is present between respective end portions of the narrow patterns that are near each other.

13. The test strip according to claim 12,
wherein the gap between the respective end portions of the narrow patterns that are near each other is a gap having a constant dimension in a width direction that is orthogonal to a longer direction of the narrow patterns.

14. The test strip according to claim 12,
wherein the arrangement of the plurality of narrow patterns forms a plurality of segments arranged in a single row along a longer direction of the substrate, and forms unit grids, on both sides of the single row, that each contains corresponding segments and that are arranged along the longer direction in an alternating manner; and
both ends of the segments arranged in the single row as a whole are conductive with the pair of wires.

15. The test strip according to claim 14,
wherein the arrangement of the plurality of narrow patterns has other unit grids that make contact with the opposite side of the segments arranged in a single row from the side on which the aforementioned unit grids are located.

16. The test strip according to claim 8,
wherein one of the terminals in the first pair of electrode terminals and one of the terminals in the second pair of electrode terminals are formed in common.

17. A manufacturing method of a test strip for manufacturing the test strip according to claim 8, the method comprising:

forming the pair of the working electrode and the counter electrode and the pair of wires on the substrate;

forming the narrow patterns of the resistance portion through screen printing and forming the insulating layer that covers the active portions of the narrow patterns aside from the end portions and that has the circular through-holes on the substrate in that order;

forming the sensor unit so as to span the space between the working electrode and the counter electrode;

finding an electrical resistance the resistance portion is to have as the attribute information including the sensitivity of the test strip by causing the sensor unit to operate; and selecting the end portions of the narrow patterns that are close to each other so that the resistance portion as a whole has the electrical resistance that has been found, and then forming the circular patterns through potting so as to overlap with the selected end portions and serve as borders of the circular through-holes in the insulating layer.

18. The manufacturing method of a test strip according to claim 17,
wherein after forming the sensor unit and before finding the electrical resistance the resistance portion is to have,
a spacer that forms side walls that face each other and a flat cover that covers the sensor unit across a space between the side walls of the spacer that face each other are provided on the substrate in order to regulate the amount of the bodily fluid that makes contact with the sensor unit on the substrate; and
the first pair and second pair of electrode terminals and the resistance portion are exposed on the substrate from the spacer and the cover.

* * * * *